US010842824B2

(12) United States Patent
Koob

(10) Patent No.: US 10,842,824 B2
(45) Date of Patent: *Nov. 24, 2020

(54) METHOD FOR INDUCING ANGIOGENESIS

(71) Applicant: MiMedx Group, Inc., Marietta, GA (US)

(72) Inventor: Thomas J. Koob, Marietta, GA (US)

(73) Assignee: MIMEDX GROUP, INC., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/039,765

(22) Filed: Jul. 19, 2018

(65) Prior Publication Data

US 2019/0022146 A1    Jan. 24, 2019

Related U.S. Application Data

(63) Continuation of application No. 14/601,075, filed on Jan. 20, 2015, now Pat. No. 10,052,351.

(60) Provisional application No. 61/928,986, filed on Jan. 17, 2014.

(51) Int. Cl.
    *A61K 35/50*    (2015.01)
    *A61L 27/36*    (2006.01)
    *A61L 27/38*    (2006.01)
    *A61L 27/54*    (2006.01)

(52) U.S. Cl.
    CPC .......... *A61K 35/50* (2013.01); *A61L 27/3604* (2013.01); *A61L 27/3804* (2013.01); *A61L 27/54* (2013.01); *A61L 2300/414* (2013.01); *A61L 2400/06* (2013.01)

(58) Field of Classification Search
    CPC .. A61K 35/50; A61L 27/3604; A61L 27/3804
    See application file for complete search history.

(56) References Cited

U.S. PATENT DOCUMENTS

| | | |
|---|---|---|
| 3,272,204 A | 9/1966 | Artandi et al. |
| 3,885,320 A | 5/1975 | Hodson et al. |
| 4,703,108 A | 10/1987 | Silver et al. |
| 4,745,771 A | 5/1988 | Linner et al. |
| 4,807,442 A | 2/1989 | Linner et al. |
| 4,847,049 A | 7/1989 | Yamamoto |
| 4,865,871 A | 9/1989 | Livesey et al. |
| 4,964,280 A | 10/1990 | Piunno et al. |
| 4,968,325 A | 11/1990 | Black et al. |
| 5,118,867 A | 6/1992 | Bahrmann et al. |
| 5,284,655 A | 2/1994 | Bogdansky et al. |
| 5,541,232 A | 7/1996 | Howell et al. |
| 5,780,295 A | 7/1998 | Livesey et al. |
| 5,807,581 A | 9/1998 | Rosenblatt et al. |
| 6,163,979 A | 12/2000 | Oetjen et al. |
| 6,565,960 B2 | 5/2003 | Koob et al. |
| 6,652,583 B2 | 11/2003 | Hopkins et al. |
| 6,716,895 B1 | 4/2004 | Terry |
| 6,893,462 B2 | 5/2005 | Buskirk et al. |
| 6,936,271 B1 | 8/2005 | Oliver et al. |
| 7,101,857 B2 | 9/2006 | Sung et al. |
| 7,311,904 B2 | 12/2007 | Hariri |
| 7,311,905 B2 | 12/2007 | Hariri |
| 7,901,455 B2 | 3/2011 | Koob et al. |
| 8,153,162 B2 | 4/2012 | Tseng et al. |
| 8,177,839 B2 | 5/2012 | Koob et al. |
| 8,192,481 B2 | 6/2012 | King |
| 8,196,416 B2 | 6/2012 | Uri et al. |
| 8,323,701 B2 | 12/2012 | Daniel et al. |
| 8,357,403 B2 | 1/2013 | Daniel et al. |
| 8,372,437 B2 | 2/2013 | Daniel |
| 8,372,439 B2 | 2/2013 | Daniel et al. |
| 8,623,421 B2 | 1/2014 | Daniel |
| 8,946,163 B2 | 2/2015 | Koob |
| 8,961,617 B2 | 2/2015 | Young |
| 10,052,351 B2 * | 8/2018 | Koob .................. A61K 35/50 |
| 2002/0019516 A1 | 2/2002 | Noff et al. |
| 2002/0160510 A1 | 10/2002 | Hariri |
| 2003/0143207 A1 | 7/2003 | Livesey et al. |
| 2003/0187515 A1 | 10/2003 | Hariri et al. |
| 2004/0048796 A1 | 3/2004 | Hariri et al. |
| 2006/0140913 A1 | 6/2006 | Bhatia |
| 2006/0166361 A1 | 7/2006 | Seyda et al. |
| 2006/0210532 A1 | 9/2006 | Carmeliet et al. |
| 2007/0020225 A1 | 1/2007 | Abramson et al. |
| 2007/0021762 A1 | 1/2007 | Liu et al. |
| 2007/0071740 A1 | 3/2007 | Tseng et al. |
| 2007/0071828 A1 | 3/2007 | Tseng et al. |
| 2007/0144062 A1 | 6/2007 | Wright |
| 2007/0160588 A1 | 7/2007 | Kihm |
| 2007/0202189 A1 | 8/2007 | Ahlfors |

(Continued)

FOREIGN PATENT DOCUMENTS

| CN | 101433556 | 5/2009 |
|---|---|---|
| EP | 0 431 479 A1 | 6/1991 |

(Continued)

OTHER PUBLICATIONS

Office Action for Australian Application No. 2015206236 dated Apr. 12, 2019.
Office Action for European Application No. 15737660.9 dated Apr. 18, 2019, 7 pages.
"MiMedx Group Announces Launch of EpiFix™ and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
Bauer S.M., et al., "Angiogenesis, vasculogenesis, and induction of healing in chronic wounds." Vascular and endovascular surgery 2005, 39:293-306.

(Continued)

Primary Examiner — Ruth A Davis
(74) Attorney, Agent, or Firm — Alston & Bird LLP

(57) ABSTRACT

Disclosed herewith is a method for inducing angiogenesis using modified placental tissue or an extract thereof to treat conditions other than cardiovascular conditions.

12 Claims, 6 Drawing Sheets

(56) References Cited

U.S. PATENT DOCUMENTS

| | | |
|---|---|---|
| 2007/0248575 A1 | 10/2007 | Connor et al. |
| 2007/0299043 A1 | 12/2007 | Hunter et al. |
| 2008/0046095 A1 | 2/2008 | Daniel |
| 2008/0069895 A1 | 3/2008 | Liu et al. |
| 2008/0181967 A1 | 7/2008 | Liu et al. |
| 2008/0193554 A1 | 8/2008 | Dua et al. |
| 2008/0233552 A1 | 9/2008 | Ma et al. |
| 2009/0012629 A1 | 1/2009 | Yao et al. |
| 2009/0053290 A1 | 2/2009 | Sand et al. |
| 2009/0056162 A1 | 3/2009 | McMahon et al. |
| 2009/0092664 A1 | 4/2009 | Mumper et al. |
| 2009/0287308 A1 | 11/2009 | Davis et al. |
| 2009/0291891 A1 | 11/2009 | Neufeld |
| 2010/0028849 A1 | 2/2010 | Shelby et al. |
| 2010/0104539 A1 | 4/2010 | Daniel et al. |
| 2010/0136114 A1 | 6/2010 | Mao |
| 2010/0199514 A1 | 8/2010 | Camisa |
| 2010/0209403 A1 | 8/2010 | Meiron et al. |
| 2010/0209408 A1 | 8/2010 | Livesey et al. |
| 2010/0260847 A1 | 10/2010 | Hariri |
| 2010/0272782 A1 | 10/2010 | Owens et al. |
| 2010/0317677 A1 | 12/2010 | Hassel et al. |
| 2011/0177150 A1 | 7/2011 | Pathak et al. |
| 2011/0189301 A1 | 8/2011 | Yang et al. |
| 2011/0206776 A1 | 8/2011 | Tom et al. |
| 2011/0223142 A1 | 9/2011 | Sanford et al. |
| 2011/0280834 A1 | 11/2011 | Forrester et al. |
| 2011/0282448 A1 | 11/2011 | Paulos et al. |
| 2011/0307059 A1 | 12/2011 | Young et al. |
| 2012/0010708 A1 | 1/2012 | Young et al. |
| 2012/0078378 A1 | 3/2012 | Daniel et al. |
| 2012/0135045 A1 | 5/2012 | Nixon et al. |
| 2012/0171180 A1 | 7/2012 | Abramson et al. |
| 2012/0189571 A1 | 7/2012 | Sengupta et al. |
| 2012/0189583 A1 | 7/2012 | Liu et al. |
| 2012/0189586 A1 | 7/2012 | Harrell |
| 2012/0282348 A1 | 11/2012 | Yates et al. |
| 2012/0294910 A1 | 11/2012 | Daniel et al. |
| 2013/0095060 A1 | 4/2013 | Hsieh et al. |
| 2013/0202676 A1 | 8/2013 | Koob et al. |
| 2013/0218274 A1 | 8/2013 | Spencer et al. |
| 2013/0230561 A1 | 9/2013 | Daniel et al. |
| 2013/0273008 A1 | 10/2013 | Lemper et al. |
| 2013/0344162 A1 | 12/2013 | Morse et al. |
| 2014/0017280 A1 | 1/2014 | Daniel et al. |
| 2014/0050788 A1 | 2/2014 | Daniel et al. |
| 2014/0051059 A1 | 2/2014 | Pringle et al. |
| 2014/0052247 A1 | 2/2014 | Daniel et al. |
| 2014/0052274 A1 | 2/2014 | Koob et al. |
| 2014/0067058 A1 | 3/2014 | Koob et al. |
| 2014/0106447 A1 | 4/2014 | Brown et al. |
| 2014/0140964 A1 | 5/2014 | Brown et al. |
| 2014/0142025 A1 | 5/2014 | Koob |
| 2014/0142041 A1 | 5/2014 | Koob |
| 2014/0205646 A1 | 7/2014 | Morse et al. |
| 2014/0255496 A1 | 9/2014 | Daniel et al. |
| 2014/0255508 A1 | 9/2014 | Morse et al. |
| 2014/0271728 A1 | 9/2014 | Koob |
| 2014/0302162 A1 | 10/2014 | Morse et al. |
| 2014/0308233 A1 | 10/2014 | Koob |
| 2014/0356451 A1 | 12/2014 | Koob |
| 2015/0010609 A1 | 1/2015 | Tom et al. |
| 2015/0010610 A1 | 1/2015 | Tom et al. |
| 2015/0127116 A1 | 5/2015 | Pringle et al. |
| 2015/0238540 A1 | 8/2015 | Koob et al. |
| 2015/0250829 A1 | 9/2015 | Daniel et al. |

FOREIGN PATENT DOCUMENTS

| | | |
|---|---|---|
| EP | 0 506 207 B1 | 9/1992 |
| JP | 2013/523152 | 6/2013 |
| KR | 10/1991-0011727 A | 8/1991 |
| KR | 10/2001/100588 | 11/2001 |
| KR | 10/2006/0057850 | 5/2006 |
| WO | WO-87/00062 A1 | 1/1987 |
| WO | WO-88/03805 A1 | 6/1988 |
| WO | WO-2009/033160 | 3/1999 |
| WO | WO-01/00151 A1 | 1/2001 |
| WO | WO-2001/08716 A1 | 2/2001 |
| WO | WO-2004/026244 | 4/2004 |
| WO | WO-2007/010305 | 1/2007 |
| WO | WO-2007/076522 | 7/2007 |
| WO | WO-2007/083984 A1 | 7/2007 |
| WO | WO-2006/025395 | 5/2008 |
| WO | WO-2009/048908 | 4/2009 |
| WO | WO-2009/132186 A1 | 10/2009 |
| WO | WO-2010/029344 A2 | 3/2010 |
| WO | WO-2011/103470 | 8/2011 |
| WO | WO-2011/127117 | 10/2011 |
| WO | WO-2012/003377 | 1/2012 |
| WO | WO-2012/065937 A1 | 5/2012 |
| WO | WO-2012/069559 A1 | 5/2012 |
| WO | WO-2012/112410 | 8/2012 |
| WO | WO-2012/112417 A2 | 8/2012 |
| WO | WO-2012/112441 A1 | 8/2012 |
| WO | WO-2013/095830 A1 | 6/2013 |
| WO | WO-2013/171752 | 11/2013 |

OTHER PUBLICATIONS

Bennett JP, et al., "Treatment of chronic ulceration of the legs with human amnion." Lancet 1980, 1:1153-1156.

Blakytny R., et al., "The molecular biology of chronic wounds and delayed healing in diabetes. Diabetic medicine" A Journal of the British Diabetic Association 2006, 23:594-608.

Borkow et al., "Reducing the risk of skin pathologies in diabetics by using copper impregnated socks", Medical Hypotheses, 2009, 1-4, doi:10.1016/j.mehy.2009.02.050.

Carmeliet, P., et al., "Synergism between vascular endothelial growth factor and placental growth factor contributes to angiogenesis and plasma extravasation in pathological conditions." Nature medicine 2001, 7:575-583.

Database WPI XP002732611 & KR 2001-0100588, dated Nov. 14, 2001—Abstract.

Dua, H.S., et al., "The amniotic membrane in ophthalmology." Survey of ophthalmology 2004, 49:51-177.

Ennis W., et al. "Clinical experience with a novel regenerative template for hard to heal wounds." In SA WC Annual Spring Meeting; Atlanta, GA. 2012.

EpiFix Product Brochure (2011).

Extended European Search Report dated Dec. 2, 2014, for European Patent Application No. EP 12746721.

Faulk W.P., et al., "Human amnion as an adjunct in wound healing." Lancet 1980, 1:1156-1158.

Forbes J, et al., "Dehydrated amniotic membrane allografts for the treatment of chronic wounds: a case series." Journal of Wound Care 2012, 21:290, 292, 294-296.

Gruss, J.S., et al. "Human amniotic membrane: a versatile wound dressing." Canadian Medical Association journal 1978, 118:1237-1246.

Hannallah et al., "Cerebrospinal fluid leaks following cervical spine surgery," J. Bone Joint Surg. Am., (2008), 90(5):1101-1105.

Hao, Y., et al., "Identification of antiangiogenic and antiinflammatory proteins in human amniotic membrane." Cornea 2000, 19:348-352.

Hattori et al., "Placental growth factor reconstitutes hematopoiesis by recruiting VEGFR1+ stem cells from bone-marrow microenvironment," Nat. Med., (2002), 8(8):841-849.

http://proxybiomedical.com/ages/ML005-0 I -Rev002.pdf (accessed on Jun. 5, 2014).

Inokuma et al., CTACK/CCL27 Accelerates Skin Regeneration via Accumulation of Bone Marrow-Derived Keratinocytes, Stem Cells, 24:2810-2916(2006).

International Preliminary Report of Patentability for PCT Application No. PCT/US14/28975 dated Feb. 6, 2015.

International Preliminary Report on Patentability for PCT Application No. PCT/US2014/012141 dated May 14, 2015.

International Search Report and Written Opinion for PCT Application No. PCT/US2012/065672, dated Feb. 8, 2013.

(56) References Cited

OTHER PUBLICATIONS

International Search Report and Written Opinion for PCT Patent Application No. PCT/US2012/024814 dated Aug. 16, 2012.
International Preliminary Report on Patentability dated Dec. 3, 2014 for PCT Patent Application No. PCT/US2013/067618.
International Preliminary Report on Patentability dated Dec. 30, 2014 for PCT Patent Application No. PCT/US13/67622.
International Preliminary Report on Patentability dated Feb. 14, 2013 for PCT Patent Application No. PCT/US12/24814.
International Preliminary Report on Patentability dated Nov. 10, 2014 for PCT Patent Application No. PCT/US2013/067623.
International Search Report and Written Opinion dated Apr. 13, 2015 for PCT Patent Application No. PCT/US15/12087.
International Search Report and Written Opinion dated Apr. 16, 2014 for PCT Patent Application No. PCT/US13/67622.
International Search Report and Written Opinion dated Apr. 21, 2014 for PCT Patent Application No. PCT/US13/67623.
International Search Report and Written Opinion dated Apr. 22, 2014 for PCT Patent Application No. PCT/US13/67618.
International Search Report and Written Opinion dated Apr. 22, 2014 for PCT Patent Application No. PCT/US13/67620.
International Search Report and Written Opinion dated Aug. 26, 2014 for PCT Patent Application No. PCT/US2014/033346.
International Search Report and Written Opinion dated Dec. 29, 2014 for PCT Patent Application PCT/US2014/053270.
International Search Report and Written Opinion dated Dec. 30, 2014 in PCT Patent Application No. PCT/US2014/054603.
International Preliminary Report on Patentability dated Feb. 1, 2013, for PCT Application No. PCT/US12/24798.
International Search Report and Written Opinion dated Jun. 20, 2012 for PCT Application No. PCT/US12/24798.
International Preliminary Report on Patentability dated Nov. 28, 2014, for PCT Application No. PCT/US2013/054319.
International Search Report and Written Opinion dated Nov. 13, 2013 for PCT Patent Application No. PCT/US2013/054319.
International Preliminary Report of Patentability for PCT Application No. PCT/US2013/054320 dated Feb. 26, 2015.
International Search Report and Written Opinion for PCT Application No. PCT/US2013/054320, dated Nov. 6, 2013.
International Preliminary Report on Patentability dated Nov. 27, 2014, for International Patent Application No. PCT/US2013/055003.
International Search Report and Written Opinion for PCT Application No. PCT/US2013/055003, dated Nov. 19, 2013.
International Preliminary Report on Patentability dated Dec. 8, 2014, for PCT Application No. PCT/US2013/054322.
International Search Report and Written Opinion for PCT Application No. PCT/US2013/054322, dated Oct. 22, 2013.
International Preliminary Report on Patentability dated Feb. 14, 2013, for PCT Application No. PCT/US2012/024814.
International Preliminary Report on Patentability dated Dec. 30, 2014, for PCT Application No. PCT/US2013/063736.
International Search Report and Written Opinion for PCT Application No. PCT/US13/63736, dated Aug. 12, 2014.
International Preliminary Report on Patentability dated Jan. 16, 2014 for PCT Patent Application No. PCT/US12/66862.
International Search Report and Written Opinion for PCT Application No. PCT/US2012/66862, dated Feb. 12, 2013.
International Preliminary Report on Patentability dated Dec. 8, 2014, for PCT Application No. PCT/US2013/054325.
International Search Report and Written Opinion for PCT Application No. PCT/US2013/054325, dated Oct. 28, 2013.
International Preliminary Report of Patentability for PCT Patent Application PCT/US2013/064146, dated Sep. 25, 2014.
International Search Report and Written Opinion dated Jan. 9, 2014 for PCT Patent Application No. PCT/US2013/064146.
International Search Report and Written Opinion for PCT Application No. PCT/US2014/012141, dated May 20, 2014.
International Search Report and Written Opinion dated Jul. 24, 2014 for PCT Patent Application No. PCT/US2014/028975.

John, T "Human amniotic membrane transplantation: past, present, and future." Ophthalmology clinics of North America 2003, 16:43-65, vi.
Kelly et al., "Disparate Effects of Similar Phenolic Phytochemicals as Inhibitors of Oxidative Damage to Cellular DNA", Mutation Res., vol. 485, pp. 309-318, (2001).
Kim, J.C., et al., "The effects on inhibition of corneal neovascularization after human amniotic membrane transplantation in severely damaged rabbit corneas. Korean journal of ophthalmology" KJO 1995, 9:32-46.
Kim, K.A., et al., "Dysfunction of endothelial progenitor cells under diabetic conditions and its underlying mechanisms." Archives of pharmacal research 2012, 35:223-234.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Koizumi, N.J., et al., "Growth factor mRNA and protein in preserved human amniotic membrane." Current eye research 2000, 20:173-177.
Koob et al., "Biological properties of dehydrated human amnion/chorion composite graft: implications for chronic wound healing," International Wound Journal, (2013), 10(5):493-500.
Kubo M., et al., "Immunogenicity of human amniotic membrane in experimental xenotransplantation." Investigative ophthalmology & visual science 2001, 42:1539-1546.
Li J., et al., "Angiogenesis in wound repair: angiogenic growth factors and the extracellular matrix." Microscopy research and technique 2003, 60:107-114.
Lopez-Valladares, M.J., et al., "Donor age and gestational age influence on growth factor levels in human amniotic membrane." Acta ophthalmologica 2010, 88:e211-216.
Lu, et al., "Molecular mechanisms and clinical applications of nordihydroguaiaretic acid (NDGA) and its derivatives: an update," Med. Sci. Monit., (2010), 16(5):RA93-RA100.
Mayfield et al., "Watertight closure of spinal note," J. Neurosurg., (1975), 43(5):639-640.
Mermet, I., et al., Use of amniotic membrane transplantation in the treatment of venous leg ulcers. Wound repair and regeneration : official publication of the Wound Healing Society [and] the European Tissue Repair Society 2007, 15:459-464.
MiMedx Press Release, "MiMedx Scientific Study is Electronically Published in the International Wound Journal", 2013.
Moussy et al., "Transport characteristics of a novel local drug delivery system using nordihydroguaiaretic acid (NDGA)-polymerized collagen fibers," Biotechnology Progress, (2007), 23(4):990-994.
MyBioSource/www.mybiosource.com/prods/Recombinant-Protein/CCL27-CTACK/datasheet.php?products-id-444088> Accessed Jun. 9, 2015).
Nagaya et al., "Transplantation of mesenchymal stem cells improves cardiac function in a rat model of dilated cardiomyopathy", Circulation, 2005, 112(8):1128-1135.
Nibbs, R., et al., "CCL27/PESKY: a novel paradigm for chemokine function,"Expert Opin. Biol. Ther., 3(1 ):15-22 (2003).
Parolini et al., "Toward cell therapy using placenta-derived cells: disease mechanisms, cell biology, preclinical studies, and regulatory aspects at the round table", Stem Cells and Development, 2010, 19(2):143-154.
Rennert et al. "Stem Cell Recruitment After Injury; Lessons for Regenerative Medicine," Regen Med. Nov. 2012; 7(6): 833-850.
Russo, A., et al., "The effects of different preservation processes on the total protein and growth factor content in a new biological product developed from human amniotic membrane." Cell and tissue banking 2012, 13:353-361.
Serena, T, et al., "Clinical Research: Dehydrated human amniotic membrane (dHAM) treatment of lower extremity venous ulceration (CR23)." In SAWC Annual Spring Meeting; Atlanta, GA. 2012.
Sheikh, E.S., et al., "Use of dehydrated human amniotic membrane allografts to promote healing in patients with refractory non healing wounds" International Wound Journal (2014), 11:711-717.
Smiell, J.M., et al., "Efficacy and safety of becaplermin (recombinant human platelet-derived growth factor-BB) in patients with

(56) References Cited

OTHER PUBLICATIONS nonhealing, lower extremity diabetic ulcers: a combined analysis of four randomized studies." Wound repair and regeneration: official publication of the Wound Healing Society [and] the European Tissue Repair Society 1999, 7:335-346.

Steed, D.L., et al. Amnion-derived cellular cytokine solution: a physiological combination of cytokines for wound healing. Eplasty 2008, 8:e18.

Subrahmanyam, M: Amniotic membrane as a cover for microskin grafts. British journal of plastic surgery 1995, 48:477-478.

Tao, et al., "Implantation of amniotic membrane to reduce postlaminectomy epidurla adhesions," Eur. Spine. J., (2009), 18:1202-1212.

Toda, A, et al., "The potential of amniotic membrane/amnion-derived cells for regeneration of various tissues." Journal of Pharmacological Sciences 2007, 105:215-228.

Tonnesen, M.G., et al., "Angiogenesis in wound healing." The journal of investigative dermatology Symposium proceedings / the Society for Investigative Dermatology, Inc. [and] European Society for Dermatological Research 2000, 5:40-46.

Uberti, M.G., et al., "Amnion-derived cellular cytokine solution (ACCS) promotes migration of keratinocytes and fibroblasts." Annals of plastic surgery 2010, 64:632-635.

Ueta, M, et al., "Immunosuppressive properties of human amniotic membrane for mixed lymphocyte reaction." Clinical and experimental immunology 2002, 129:464-470.

Ventura, et al. "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts," The Journal of Biological Chemistry, 282 (2007) 14243-14254.

Waterman et al. "A New Mesenchymal Stem Cell (Msc) Paradigm: Polarization Into a Pro-Inflammatory Msc1 or an Immunosuppressive Msc2 Phenotype"; PLos One 5(4); Apr. 2010, pp. 1-14.

Werner S. et al."Regulation of wound healing by growth factors and cytokines." Physiological reviews 2003, 83:835-870.

Wieman, T.J., et al., "Efficacy and safety of a topical gel formulation of recombinant human platelet-derived growth factor-BB (becaplermin) in patients with chronic neuropathic diabetic ulcers. A phase III randomized placebo-controlled double-blind study." Diabetes care 1998, 21:822-827.

Zaja-Milatovic, S., et al., "CXC chemokines and their receptors: A case for a significant biological role in cutaneous wound healing," Histol. Histopathol., 23(11):1399-1407 (2008).

Zelen, C.M., et al. "A prospective randomised comparative parallel study of amniotic membrane wound graft in the management of diabetic foot ulcers." International wound journal 2013, 10:502-507.

Partial European Search Report dated Oct. 2, 2017 in related European Patent Application No. 15737660.9.

European Search Report dated Jan. 15, 2018 in related European Patent Application No. 15737660.9.

"Complaint for Violations of the Federal Securities Laws" Spencer Abrams vs. Mimedx Group, (Sep. 14, 2013), pp. 1-30.

"EpiFix, Scientific & Clinical Compendium" (Mar. 2013), pp. 1-11.

Office Action for Japanese Application No. 2016-544820 dated Nov. 29, 2018.

MiMedx Group, "PURION Processed Dehydrated Human Amnion/Chorion Membrane Allografts," pp. 1-12, (2012).

Article 94(3) Communication for European Application No. 15737660.9 dated Feb. 11, 2020, 6 pages.

* cited by examiner (a) Angiogenin (b) HB-EGF (c) PDGF-BB (d) IL-2

(e) IL-6

(f) IL-8

METHOD FOR INDUCING ANGIOGENESIS

CROSS-REFERENCE TO RELATED APPLICATIONS

This application is a continuation of U.S. patent application Ser. No. 14/601,075, filed Jan. 20, 2015, which claims benefit from U.S. Provisional Application No. 61/928,986, filed Jan. 17, 2014, each of which is hereby incorporated by reference in its entirety.

FIELD OF THE INVENTION

The present application relates to methods for inducing angiogenesis using modified placental tissue or extracts thereof to treat conditions other than cardiovascular conditions.

BACKGROUND OF THE INVENTION

Tissue regeneration and wound healing require interactions among distinct resident cell types, as well as inflammatory cells, platelets, and stem cells. Particularly, chronic wounds are associated with a number of deficiencies in critical wound healing processes, including growth factor signaling and neovascularization.

Regenerative medicine is a relatively new therapy that allows the body to repair, replace, restore and regenerate damaged or diseased cells, tissues and organs. Conventional regenerative therapies include cell therapy, tissue engineering, biomaterial engineering, growth factor treatment, and transplantation. Regenerative therapies are promising remedies for numerous non-cardiovascular diseases and disorders. However, the clinical potential of many of these regenerative therapies cannot be fully realized without a functioning vasculature to provide essential cells and bioactive agents, oxygen and nutrient supply, as well as to evacuate accumulating metabolic products.

To date, suitable neovascularization remains an unresolved issue hampering the progress of regenerative medicine, wound healing and treatment of other non-cardiovascular conditions. The present invention provides a novel and promising therapy to induce angiogenesis necessary for tissue regeneration, wound healing and, in particular, for treating non-cardiovascular conditions.

SUMMARY OF THE INVENTION

Angiogenesis is contemplated as a valuable treatment in numerous non-cardiovascular conditions, including mitigating or inhibiting peripheral neuropathy in diabetic patients, cirrhosis where scars block the blood flow through the liver, pulmonary conditions such as cystic fibrosis, pulmonary fibrosis, chronic obstructive pulmonary disease (COPD), and non-cardiovascular ischemia such as bone necrosis, limb ischemia, etc.

In one aspect of the invention, there is provided a method for inducing angiogenesis in a non-cardiovascular body region of a subject in need thereof comprising delivering an effective amount of a composition comprising modified placental tissue to said non-cardiovascular body region.

In one aspect of the invention, there is provided a method for inducing angiogenesis in a non-cardiovascular body region of a subject in need thereof comprising delivering an effective amount of a composition comprising placental growth factors and/or stem cells extracted from placental tissue to said non-cardiovascular body region.

In another aspect of the invention, there is provided a method for inducing angiogenesis in a non-cardiovascular body region of a subject wherein blood to said region is restricted due to injury or disease which method comprises injecting an effective amount of an aqueous solution comprising micronized modified placental tissue to said non-cardiovascular body region and maintaining said region under conditions wherein angiogenesis is induced.

In some embodiments, blood flow to the non-cardiovascular body region is restricted, for example, due to vascular damage arising from injury and/or disease.

In some embodiments, the non-cardiovascular body regions include liver, lung, nerve, bone, or skin. Restricted blood flow to peripheral portions of the body include, for example, limbs, hands, or feet.

In some embodiments, the subject has or is at risk of developing peripheral neuropathy, cirrhosis, a pulmonary condition, or other non-cardiovascular conditions. In some embodiments, the pulmonary condition may be, for example, cystic fibrosis, pulmonary fibrosis, or chronic obstructive pulmonary disease (COPD). In some embodiments, the non-cardiovascular conditions may be, for example, bone necrosis, ischemia, organ injury, tissue injury, or a chronic wound. The ischemia may be, for example, limb ischemia. In one embodiment, the subject in need thereof suffers from a non-cardiovascular condition or is at risk of developing a condition that can be treated or ameliorated by promoting angiogenesis. Exemplary conditions relating to non-cardiovascular conditions include, but are not limited to, an injury to the skin, tissue, or organ, ischemia, chronic wounds associated with systemic disease such as diabetes or non-cardiovascular atherosclerosis.

In some embodiments, the modified placental tissue comprises one or more of isolated amnion, isolated chorion, isolated amnion and isolated chorion laminated together in any configuration and in any number, Wharton's jelly, isolated amniotic epithelial layer, or any combination thereof. In some embodiments the modified placental tissue is a tissue graft. In other embodiments, the modified placental tissue is micronized. Moreover, the modified placental tissue can be further processed to form a dehydrated graft or an extract of the modified placental tissue. It is within the purview of one skilled in the art to select a pharmaceutically and/or physiologically suitable extracting solution, such as water, saline and phosphate buffered saline (PBS).

In some embodiments, the composition is injectable. In other embodiments, the composition is a liquid, gel, or paste. In still other embodiments, the composition is employed by a nebulizer. It is within the purview of one skilled in the art to select a pharmaceutically and/or physiologically suitable excipient, such as an aqueous or non-aqueous excipient. It is also within the purview of one skilled in the art to use micronized or non-micronized modified placental tissue. Where micronized placental tissue is used, one of skill in the art can also determine the appropriate size of the micronized particles for the specific application.

In some embodiments, the method of this invention employs injectable composition comprising micronized placental tissue, described in detail in PCT Application No. PCT/US2012/024798, filed on Feb. 13, 2012, the content of which is incorporated by reference in its entirety. In other embodiments, beneficial ingredients such as growth factors and stem cells are extracted from the placental tissue and the extract is used for treatment. Preferably, the extract can be employed by a nebulizer. It is contemplated that when the placental tissue is micronized, fine particles, e.g., particles having a particle size of being capable of nebulization, such as less than about 200 nm, can be directly applied through a nebulizer.

It is contemplated that any placental tissue or any composition comprising placental or umbilical cord tissue can be used in the methods of this invention. Preferred placental tissues are, for example, AmnioFix® and EpiFix® tissue grafts(commercially available from MiMedx Group, Inc., Marietta, Ga., USA). Non-limiting examples of compositions and tissue grafts that can be used with the embodiments described herein, and methods of obtaining placental tissue grafts are described in detail in U.S. Pat. No. 8,372,437, entitled "Improved Placental Tissue Grafts," and U.S. Pat. No. 8,357,403, entitled "Placental tissue grafts and improved methods of preparing and using the same," both assigned to MiMedx Group, Inc. The content of each patent is incorporated by reference in its entirety for all of its methods, compositions and materials.

In one aspect, the invention relates to a method for inducing angiogenesis by providing a subject in need thereof an effective amount of a composition comprising modified placental tissue, which comprises one or more angiogenic growth factors such as angiogenin, angiopoietin-2 (ANG-2), epidermal growth factor (EGF), basic fibroblast growth factor (bFGF), heparin binding epidermal growth factor (HB-EGF), hepatocyte growth factor (HGF), leptin, platelet derived growth factor AA (PDGF-AA), platelet derived growth factor BB (PDGF-BB), placental growth factor (P1GF), vascular endothelial growth factor (VEGF), keratinocyte growth factor (KGF), TGF-α and -β, nerve growth factor (NGF), and granulocyte colony-stimulating factor (GCSF).

In a related aspect, the present invention relates to a method for producing a composition comprising modified placental tissue, which comprises one or more angiogenic growth factors such as angiogenin, angiopoietin-2 (ANG-2), epidermal growth factor (EGF), basic fibroblast growth factor (bFGF), heparin binding epidermal growth factor (HB-EGF), hepatocyte growth factor (HGF), leptin, platelet derived growth factor AA (PDGF-AA), platelet derived growth factor BB (PDGF-BB), placental growth factor (P1GF), and vascular endothelial growth factor (VEGF), keratinocyte growth factor (KGF), TGF-α and -β, and nerve growth factor (NGF), and granulocyte colony-stimulating factor (GCSF). The method comprising the step of cleaning and separating one or more of amnion membrane, chorion membrane and amniotic epithelial layer from a placenta obtained from a healthy donor. The method further comprises one or more optional steps of decellularizing the separated membrane, micronizing the modified placental tissue, dehydrating the modified placental tissue, and/or extracting the modified placental tissue using at least one pharmaceutically and/or physiologically suitable extracting solutions.

BRIEF DESCRIPTION OF THE DRAWINGS

The accompanying drawings, which are incorporated in and constitute a part of this specification, illustrate several aspects described below.

DETAILED DESCRIPTION

Figure 1:
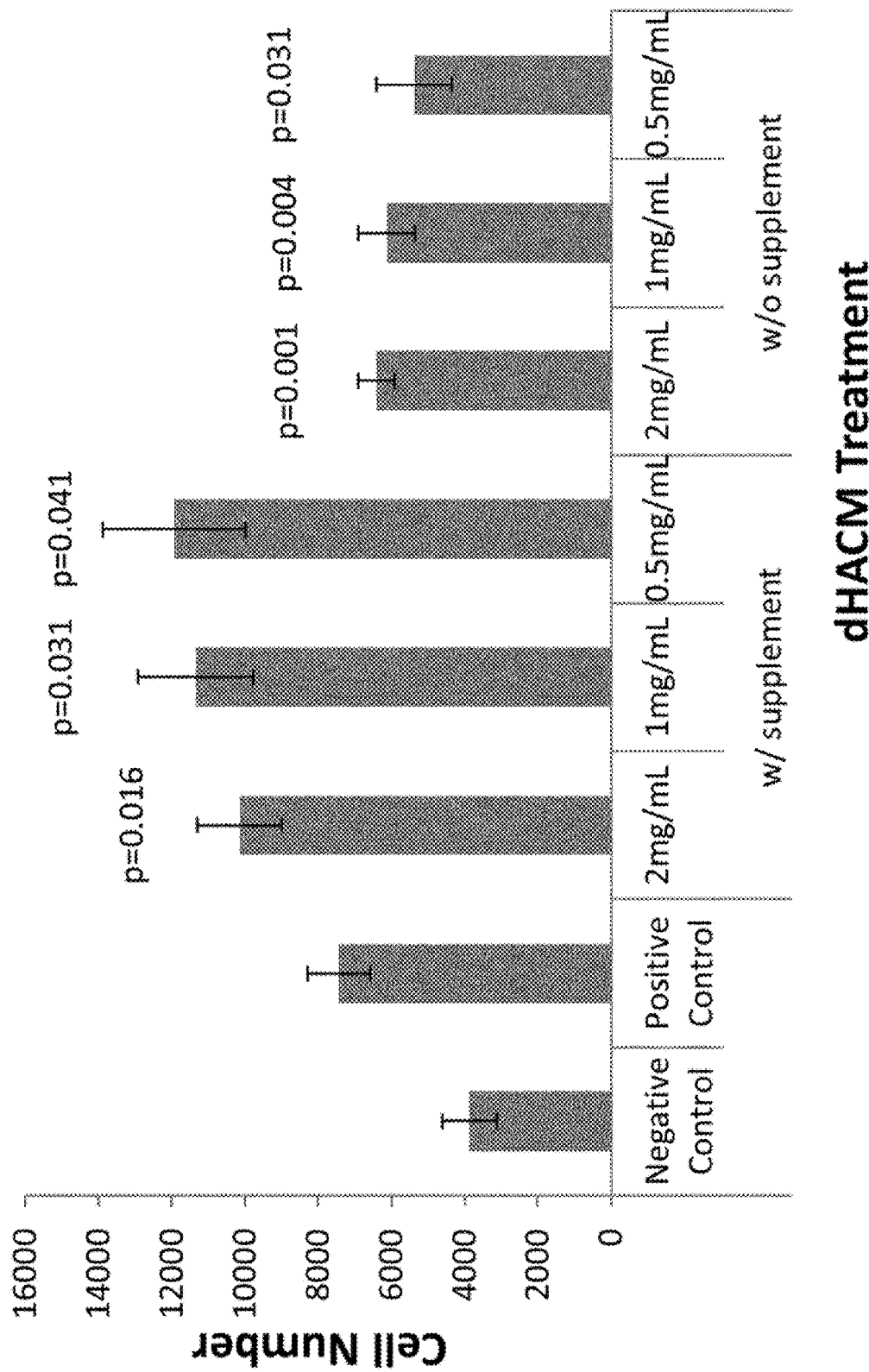
FIG. 1 shows the effects of extracts of dHACM on microvascular endothelial cell proliferation in vitro. dHACM extracts promoted proliferation of HMVECs over controls; however, no dose response was observed at these concentrations. The p values shown indicate statistical significance from their respective controls. Values shown are means±standard deviation (n=5).

Before this invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" or "patient" as used herein refers to any vertebrate organism including, but not limited to, mammalian subjects such as humans, farm animals, domesticated pets and the like.

The term "amnion" as used herein includes amniotic membrane where the intermediate tissue layer has been substantially removed.

The term "biocompatible" as used herein refers to a material that is suitable for implantation or injection into a subject. In various aspects, a biocompatible material does not cause toxic or injurious effects once implanted in the subject.

The term "modified placental tissue" refers to any and all components of placental tissue (excluding the entire placenta) that has been modified by cleaning, disinfecting, and/or segmenting the tissue as well as to separated components of placental tissue such as amnion, chorion, isolated amniotic tissue, the umbilical cord, the umbilical cord components (e.g., Wharton's jelly, umbilical cord vein and artery, and surrounding membrane) and the like. Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "extract of or "extracted from" placental tissue or the like a refers to a composition, such as a solution or a lyophilized solid comprising, or method of obtaining, one or more of the biological factors present in a placental tissue or modified placental tissue and substantially free of the placental tissue or cell materials. Such extracts included those described in U.S. patent application Ser. No. 13/744,331, U.S. patent application Ser. No. 14/157,445, or U.S. Patent Application 61/849,838 and can be prepared according to methods described therein. The patent applications are hereby incorporated by reference in their entirety.

The term "sufficient amount" or "effective amount" refers to an amount of a modified placental tissue or an extract of placental tissue that is sufficient to inhibit or treat conditions such as peripheral neuropathy, cirrhosis, cystic fibrosis, pulmonary fibrosis, chronic obstructive pulmonary disease, bone necrosis, ischemia, injury to the skin, tissue or organ, or chronic wounds, and the like. The "sufficient amount" will vary depending on a variety of factors, such as but not limited to, the type and/or amount of the placental tissue or extract of a placental tissue used, the type and/or size of the diseased or injured non-cardiac tissue to be treated, the severity of the disease or injury to the diseased or injured non-cardiac tissue to be treated and the administration route. The determination of a "sufficient amount" can be made by one of ordinary skill in the art based on the disclosure provided herein.

The term "placental growth factors" refers to that array of growth factors obtainable from modified placental tissue. The manner of obtaining such growth factors is not critical to the invention and include, by way of example only, aqueous extraction from the placenta, culturing of placental cells expressing such growth factors, and the like. The concentration of extracted growth factors can be increased by reducing the volume of water, saline, or buffer used to extract the growth factors, by addition of growth factors produced from placental cell cultures, and the like.

The term "placental tissue graft" or "tissue graft" refers to any combination of placental tissue which contains either an amnion or a chorion layer and optionally additional layers which may or may not be obtained from the placenta. Preferably, the placental tissue graft lacks an intermediate layer. Single layers of amnion or chorion can be used. However, multiple layers of amnion and/or chorion form the tissue graft, which layers are typically dehydrated and laminated together. The amnion can optionally be partially or completely decellularized such as by removing substantially all of the epithelial layer and/or the fibroblast layer. Examples of placental tissue grafts suitable for this invention include by way of example U.S. Pat. Nos. 8,323,701; 8,372,437; and U.S. Patent Publication Nos. 2014/0052247; 2014/0067058; 2014/0205646; and 2013/0202676.

The term "exogenous" refers to substances that are not naturally occurring to a body part being treated, including allograft tissue, such as modified placental tissue.

The term "endogenous" refers to autologous biological substances from a subject.

The terms "deliver, "delivered, "delivering" refers to methods of administering the compositions of the present invention. The compositions of the present invention can be delivered in a variety of ways, including topically, parenterally, intravenously, intradermally, intramuscularly, colonically, rectally or intraperitoneally. The compositions can also be administered as part of a pharmaceutical formulation.

Titles or subtitles may be used in the specification for the convenience of a reader, which are not intended to influence the scope of the present invention. Additionally, some terms used in this specification are more specifically defined below.

Placental Tissue Compositions and Methods for Making Thereof

Described herein are compositions composed placental tissue components, including micronized placental tissue components. Preferred compositions can be prepared by the exemplary route described below. Compositions may be prepared from micronized placental tissue components, which are described in PCT Application No. PCT/US12/24798, as well as in U.S. provisional application Ser. Nos. 61/442,34, 61/543,995, and 61/683,700. The contents of these applications are specifically incorporated by reference in their entireties. It is understood that the term "micronized" is meant to include micron and sub-micron sized placental tissue particles.

Figure 6:
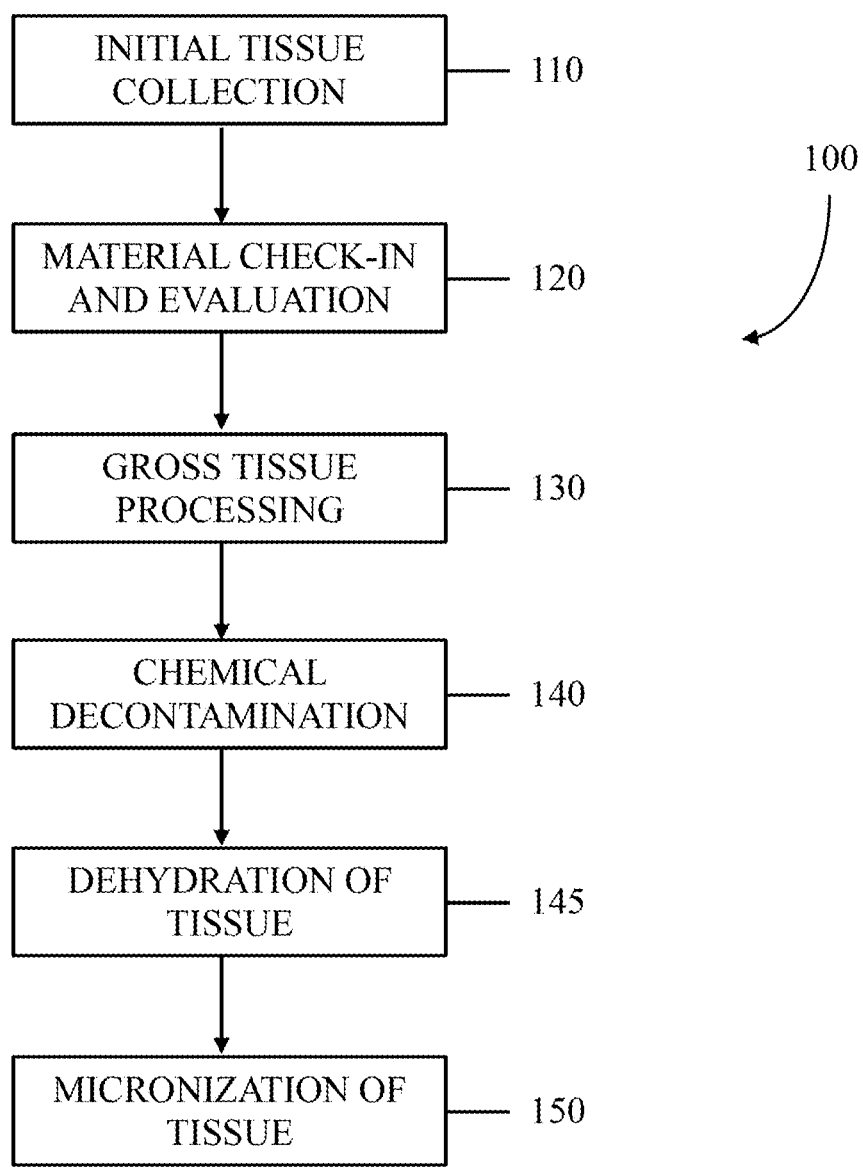
FIG. 6 is an overview flow chart of the process for making the compositions described herein.

A brief overview of certain aspects of the steps to harvest, process, and prepare placental material for later use as a placental tissue composition are described below and depicted in FIG. 6. More detailed descriptions and discussion regarding each individual step will follow. Initially, the placenta tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the amnion and chorion then takes place (step 130). Acceptable tissue is then decontaminated (step 140) and dehydrated (step 145). After decontamination and dehydration, the placental tissue components (e.g., amnion, Wharton's jelly and/or chorion individually or as grafts) are optionally then micronized (step 150). Each step is described in detail below.

Initial Tissue Collection (Step 110)

The components used to produce the micronized placental tissue are derived from the placenta. The source of the placenta can vary. In one aspect, the placenta is derived from a mammal, such as human. Other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the placental components, as will be appreciated by those skilled in the art.

Based upon a review of the donor's information and screening test results, the donor will either be deemed acceptable or not. In addition, at the time of delivery, cultures are taken to determine the presence of bacteria, for example, Clostridium or Streptococcus. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue are assembled in a staging area in a controlled (i.e., aseptic) environment and are prepared for introduction into the controlled environment. In one aspect, the placenta is processed at room temperature. If the controlled environment is a manufacturing hood, the sterile supplies are opened and placed into the hood using conventional aseptic techniques. If the controlled environment is a clean room, the sterile supplies are opened and placed on a cart covered by a sterile drape. All the work surfaces are covered by a piece of sterile drape using conventional aseptic technique, and the sterile supplies and the processing equipment are placed onto the sterile drape, again using conventional aseptic technique.

Processing equipment is decontaminated according to conventional and industry-approved decontamination procedures and then introduced into the controlled environment. The equipment is strategically placed within the controlled environment to minimize the chance for the equipment to come in proximity to or be inadvertently contaminated by the tissue specimen.

Next, the placenta is removed from the sterile shipment bag and transferred aseptically to a sterile processing basin within the controlled environment. The sterile basin contains hypertonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below. Not wishing to be bound by theory, the removal of the intermediate layer can accelerate the drying of the tissue graft, particularly if multiple amnion membranes are used to produce the graft.

Methods described herein allow for retention or removal of substantially all or some of the cellular components of the amnion layers. Removal of cellular components is a technique referred to in the art as "decellularization." Decellularization generally involves the physical and/or chemical removal of all cells present in the amnion, which includes epithelial cells and fibroblast cells. In certain aspects, the amnion is completely decellularized (e.g., removal of epithelial and fibroblast cells). In other aspects, only the epithelial layer or a portion thereof is removed. In yet other aspects, only the fibroblast layer is removed. Optionally, all cellular components are present.

In certain aspects, either a portion of the epithelial layer present on the amnion or substantially all of the epithelial layer is removed in order to expose some or most of the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

In one embodiment, the epithelial layer can be removed by techniques known in the art. For example, the epithelial layer can be scraped off of the amnion using a cell scraper. Other techniques include, but are not limited to, freezing the membrane, physical removal using a cell scraper, or exposing the epithelial cells to nonionic detergents, anionic detergents, and nucleases. The amount of epithelial layer removed ranges from 0 percent (i.e., the epithelial layer is retained) up to substantially all of the epithelial layer is removed. Intermediate amounts of epithelial layer removal can be achieved by preparing rows of epithelial layer removal intermixed with rows where the epithelial layer is retained. Alternatively, a portion of the epithelial layer is removed while the remainder is retained.

The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is placed onto a standard slide, stained with Eosin Y and viewed under the microscope. If epithelium is present, it will appear as cobblestone-shaped cells.

Chemical Decontamination (Step 140)

The placental tissue components isolated above can be chemically decontaminated using the techniques described below. In one aspect, the amnion and chorion is decontaminated at room temperature. In one aspect, the amnion produced in step 130 can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/aseptic environment and opened. Using sterile forceps or by aseptically decanting the contents, the amnion is gently removed from the Nalgene jar containing the 18% hypertonic saline solution and placed into an empty Nalgene jar. This empty Nalgene jar with the amnion is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/aseptic environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

Dehydration (145)

In one aspect, the amnion, chorion, Wharton's jelly, or any combination thereof can be processed into tissue grafts (i.e., laminates) that are subsequently micronized. In another aspect, the individual amnion, chorion, Wharton's jelly layers can be dehydrated independently and subsequently micronized alone or as a mixture of components. In one aspect, the tissue (i.e., individual membrane or graft) is dehydrated by chemical dehydration followed by freeze-drying. In one aspect, the chemical dehydration step is performed by contacting the amnion, chorion, and/or Wharton's jelly with a polar organic solvent for a sufficient time and amount in order to substantially (i.e., greater than 90%, greater than 95%, or greater than 99%) or completely remove residual water present in the tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below. After chemical dehydration, the tissue is freeze-dried in order to remove any residual water and polar organic solvent. In one aspect, the amnion, chorion, and/or Wharton's jelly can be laid on a suitable drying fixture prior to freeze-drying. For example, one or more strips of amnion can be laid on a suitable drying fixture. Next, chorion is laid on top of the amnion. In this aspect, an amnion/chorion tissue graft is produced. Alternatively, a strip of amnion can be placed on a first drying fixture, and a strip of chorion can be placed on a second drying fixture. The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga., USA. Any other suitable material that is heat and cut resistant, capable of being formed into an appropriate shape to receive wet tissue can also be used for the drying fixture.

Once the tissue is placed on the drying fixture, the drying fixture is placed in the freeze-dryer. The use of the freeze-dryer to dehydrate the tissue can be more efficient and thorough compared to other techniques such as thermal dehydration. In general, it is desirable to avoid ice crystal formation in the placental tissue as this may damage the extracellular matrix in the tissue. By chemically dehydrating the placental tissue prior to freeze-drying, this problem can be avoided.

In another aspect, the dehydration step involves applying heat to the tissue. In one aspect, the amnion, chorion, and/or Wharton's jelly is laid on a suitable drying fixture (either as individual strips or as a laminate discussed above), and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 to 120 minutes. In one aspect, the heating step can be performed at 45 minutes at a temperature of approximately 45 degrees Celcius to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

Preparation of Micronized Compositions (Step 150)

Once the amnion, chorion, and/or Wharton's jelly layer have been dehydrated individually or in the form of a tissue graft, the dehydrated tissue(s) can optionally be micronized. The micronized compositions can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 µm, less than 400 µm, less than 300 µm, or from 25 µm to 300 µm, from 25 µm to 200 µm, or from 25 µm to 150 µm. In certain aspects, particles having a larger diameter (e.g. 150 µm to 350 µm) are desirable. In other aspects, particles having a smaller diameter are desirable, for example, when particles will be employed by a nebulizer. The skill artisan would understand that the particle sizes and size ranges of the materials in the micronized composition of the present invention are the average particle size.

In one aspect, micronization is performed by mechanical grinding or shredding. In another aspect, micronization is performed by cryogenic grinding. In this aspect, the grinding jar containing the tissue is continually cooled with liquid nitrogen from the integrated cooling system before and during the grinding process. Thus the sample is embrittled and volatile components are preserved. Moreover, the denaturing of proteins in the amnion, Wharton's jelly, and/or chorion is minimized or prevented. In one aspect, the CryoMill manufactured by Retsch can be used in this aspect.

The selection of placental tissue components used to make the compositions described herein can vary depending upon the end-use of the composition. For example, placental tissue or individual components such as amnion, chorion, intermediate tissue layer, Wharton's jelly or any combination thereof can be admixed with one another and subsequently micronized. In another aspect, one or more tissue grafts composed of one or more placental tissue, amnion, chorion, Wharton's jelly layers, or any combination thereof (i.e., laminates) can be micronized. In a further aspect, one or more tissue grafts composed of one or more amnion, chorion, Wharton's jelly layer, or any combination thereof can be admixed with amnion, chorion, Wharton's jelly layer, or any combination thereof as individual components and subsequently micronized.

The amount of different components used to make the micronized compositions described herein can vary depending upon the application of the micronized composition. In one aspect, when the micronized composition is composed of amnion (with or without the intermediate tissue layer) and Wharton's jelly, the weight ratio of amnion to Wharton's jelly is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1. In another aspect, when the micronized composition is composed of amnion (with or without the intermediate tissue layer) and chorion, the weight ratio of chorion to amnion is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1.

Separation of particle sizes can be achieved by fractionation of the micronized material in sterile water by forming a suspension of particles. The upper most portion of the suspension will contain predominately the smallest particles and the lower most portion of the suspension will contain predominantly the heaviest particles. Fractionation leads to particle size separation and repeated fractionation will lead to separation of the micronized particles into varying sizes. The so separated particles can be recombined in the desired ratio of particle size as is most appropriate for making the placental tissue composition and the desired application.

In a further aspect, the placental tissues can be cross-linked. For example, a cross-linking agent can be added to the composition (e.g., amnion, chorion, Wharton's jelly, or any combination thereof as individual components and/or as tissue grafts) prior to and/or after micronization. In general, the cross-linking agent is nontoxic and non-immunogenic.

When the amnion, Wharton's jelly, and/or chorion (or a tissue graft thereof) are treated with the cross-linking agent, the cross-linking agent can be the same or different. In one aspect, the amnion, Wharton's jelly, and chorion can be treated separately with a cross-linking agent or, in the alternative, the amnion, Wharton's jelly, and chorion can be treated together with the same cross-linking agent. In certain aspects, the amnion, Wharton's jelly, and chorion can be treated with two or more different cross-linking agents. The conditions for treating the amnion, Wharton's jelly, and chorion can vary. In other aspects, the amnion, Wharton's jelly, and/or chorion can be micronized, and the micronized composition can subsequently be treated with a cross-linking agent. In one aspect, the concentration of the cross-linking agent is from 0.1 M to 5 M, 0.1 M to 4M, 0.1 M to 3 M, 0.1 M to 2 M, or 0.1 M to 1 M.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-343-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the amnion, Wharton's jelly, and chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof.

In certain aspects, the micronized compositions described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. Additionally, the pharmaceutical compositions can include carriers, thickeners, diluents, preservatives, surface active agents and the like in addition to the compounds described herein.

It will be appreciated that the actual preferred amounts of micronized placental tissue components in a specified instance will vary according to the specific utility of the composition, the particular compositions formulated, the mode of application, and the particular situs and subject being treated. Dosages for a given subject can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

In certain aspects additional components may be added to the compositions. The additional components may be fillers, bioactive agents, adhesives, stabilizers, buffers, pharmaceutical components, coloring agent, a disintegrating agent, or the like.

In another aspect, a bioactive agent can be added to the composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the composition with bioactive agent to the region of interest, the bioactive agent is delivered to the region over time. Thus, the micronized particles described herein are useful as delivery devices of bioactive agents and other pharmaceutical agents when administered to a subject. Release profiles can be modified based on, among other things, the selection of the components used to make the micronized compositions as well as the size of the particles.

In other aspects, one or more adhesives can be admixed with the compositions. Examples of such adhesives include, but are not limited to, fibrin sealants, cyanoacrylates, gelatin and thrombin products, polyethylene glycol polymer, albumin, and glutaraldehyde products. In one aspect, a coloring agent is added to facilitate in locating and properly placing the placental tissue component composition to the intended treatment site. In another aspect, a disintegrating agent modifies the rate that the placental tissue component composition erodes or disintegrates in vivo after being introduced to a subject.

In yet another aspect, the composition is admixed with at least one plasticizer. One skilled in the art would select a suitable plasticizer based on the biocompatibility of the plasticizer, effect of plasticizer on the degradation or erosion rate of the placental tissue graft in vivo, effect of the plasticizer on the properties of the mixture to facilitate flexibility and coherency of the placental tissue component composition. Exemplary plasticizers include, but are not limited to, polyethylene glycol, glucose monoesters and partial fatty acid esters, and the like.

The compositions described herein can be administered in numerous ways depending on whether local or systemic treatment is desired, and on the area to be treated. In one aspect, administration can be by injection. In other aspects the compositions is a liquid, gel or paste. In other aspects, the composition can be formulated to be applied internally to a subject. In other aspects, the composition can be applied topically (including ophthalmically, vaginally, rectally, intranasally, orally, or directly to the skin). In other aspects the compositions can be administered by a nebulizer.

In one aspect, the compositions can be formulated as a topical composition applied directly to the skin. Formulations for topical administration can include, emulsions, creams, aqueous solutions, oils, ointments, putty, pastes, gels, lotions, milks and suspensions. In one aspect, the topical composition can include one or more surfactants and/or emulsifiers.

Surfactants (or surface-active substances) that may be present are anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, alpha-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In one aspect, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In one aspect, the emulsifier can be a nonionogenic surfactant selected from the following: addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical; alkyl and/or alkenyl oligoglycosides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; and block copolymers, e.g. polyethylene glycol-30 dipolyhydroxystearates. In one aspect, the emulsifier is a polyalkylene glycol such as, for example, polyethylene glycol or polypropylene glycol. In another aspect, the emulsifier is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In another aspect, the emulsifier is a poloxamer. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula

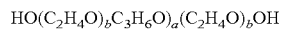

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, Pluronic® F68, P103, P105, P123, F127, and L121.

In another aspect, the emulsifier is composed of one or more fatty alcohols. In one aspect, the fatty alcohol is a liner or branched C6 to C35 fatty alcohol. Examples of fatty alcohols include, but are not limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol) elaidolinolenyl alcohol (9E, 12E, 15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), or cetearyl alcohol.

In one aspect, the carrier used to produce the topical composition is a mixture polyethylene and one or more fatty alcohols. For example, the carrier is composed of 50% to 99% by weight, 75% to 99% by weight, 90% to 99% by weight, or about 95% by weight polyethylene glycol and 1% to 50% by weight, 1% to 25% by weight, 1% to 10% by weight, or about 5% by weight fatty alcohol. In a further aspect, the carrier is a mixture of polyethylene glycol and cetyl alcohol.

The topical compositions can also include additional components typically present in such compositions. In one aspect, the topical composition can include one or more of the following components: fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, swelling agents, insect repellents, hydrotropes, solubilizers, preservatives, perfume oils and dyes. Examples of each of these components are disclosed in U.S. Pat. No. 8,067,044, which is incorporated by reference with respect these components.

The topical compositions described herein can be prepared by mixing compositions with the carrier. In the case when the carrier is composed of two or more components, the components can be admixed with one another prior to the addition of the compositions. The amount of placental tissue or placental growth factors and/or stem cells present in the topical composition can vary depending upon the application. In one aspect, the placental tissue component composition is from 0.5% to 20%, 1% to 10%, 2% to 5%, or about 3% by weight of the topical composition.

After preparation, the compositions can be immediately used or properly packaged for storage and later use.

Placental Tissue Extracts

One aspect of the invention, provides a method for inducing angiogenesis by providing a subject in need thereof of an effective amount of a composition comprising placental growth factors and/or stem cells extracted from placental tissue. Such extracts included those described in U.S. patent application Ser. No. 13/744,331, U.S. patent application Ser. No. 14/157,445, U.S. Patent Application 61/849,838 and can be prepared according to methods described therein. The patent applications are hereby incorporated by reference in their entirety.

In one embodiment, the growth factors are extracted from the placental tissue or components thereof by extraction via a pH gradient elution. The pH gradient is preferably a physiological pH gradient, for example, a pH gradient of about pH 5 to about pH 8.

Applications of Placental Tissue Components or Placental Tissue Extracts

The compositions as described herein can be used in numerous medical applications involving treating or preventing peripheral neuropathy, cirrhosis, a pulmonary condition, or non-cardiovascular conditions. In some embodiments, the pulmonary condition is cystic fibrosis, pulmonary fibrosis, or chronic obstructive pulmonary disease. In some embodiments, the non-cardiovascular condition is bone necrosis, ischemia, injury to the skin, tissue or organ, or chronic wounds.

One aspect of the invention provides a method for inducing angiogenesis in a non-cardiovascular body region of a subject wherein blood to said region is restricted due to injury or disease. The method comprises injecting an effective amount of an aqueous solution comprising micronized modified placental tissue to said non-cardiovascular body region and maintaining said region under conditions wherein angiogenesis is induced. The non-cardiovascular body region includes, for example, peripheral portions of the body, liver, lung, nerve, bone, or skin.

The composition comprising a modified placental tissue or extracts thereof described herein can be implanted proximal or internal to a diseased and/or injured non-cardiovascular body region in an amount sufficient to induce angiogenesis. In various aspects, in order to induce angiogenesis at or near a damaged non-cardiovascular body region, a sufficient amount of placental tissue or extract is required before induction of angiogenesis.

In some embodiments it is contemplated that the methods to induce angiogenesis could be used prophylactically, preferably in a diabetic subject whose diabetes is under poor control and at significant risk of developing peripheral neuropathy. Accordingly, in one embodiment, there is prophylactic treatment of a diabetic subject by delivering to the subject an effective amount of a composition comprising modified placental tissue or placental growth factors and/or stem cells therefrom to peripheral portions of the body of the diabetic subject.

It will be appreciated that the actual amounts of placental tissue or placental tissue extract administered in a specified case will vary according to the specific non-cardiovascular body region to be treated, the particular compositions formulated, the mode of application, and the degree of disease or injury in particular subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999)).

To maintain a non-cardiovascular body region under conditions to induce angiogenesis means that the subject and/or said body region may need to be immobilized, fully or partially, or restricted for a period of time sufficient to induce angiogenesis and in such a way so that the composition of modified placental tissue or placental tissue extract is retained at the site where angiogenesis is desired. For example, when inducing angiogenesis at a peripheral portion of the body such as a foot, it may be necessary for the subject to remain off his or her feet for all, substantially all, or for some of the treatment period in order for the composition to remain at the appropriate site for proper induction of angiogenesis to occur.

The following examples are put forth so as to provide those of ordinary skill in the art with a complete disclosure and description of how compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

EXAMPLES

Example 1

Angiogenic Properties of Dehydrated Human Amnionichorion Allografts: Therapeutic Potential for Soft Tissue Repair and Regeneration Normal wound healing is a complex biological process requiring interactions among distinct resident cell types, as well as inflammatory cells, platelets, and stem cells (1). Growth of new blood vessels into the wound through angiogenesis is a critical aspect of this process, to promote the adequate delivery of nutrients and regulatory factors required for tissue remodeling and regeneration (2).

The term angiogenesis describes the growth of new blood vessels from preexisting ones (2) After acute tissue injury, there is a rapid cascade of events involving the local release of angiogenic cytokines, including vascular endothelial growth factor (VEGF), placental growth factor (P1GF), platelet-derived growth factor (PDGF), basic fibroblast growth factor (bFGF), transforming growth factor β (TGF-(3), angiogenin, angiopoietin, and other factors (2,3) by damaged cells and platelets. These factors lead to rapid destabilization of local preexisting vessels and activation of local endothelial cells, a process amplified by further release of growth factors from monocytes, macrophages, and fibroblasts. The concentration gradient of angiogenic signals guides activated endothelial cells to proliferate, migrate, sprout, and invade the extracellular matrix (ECM) in coordinated fashion, whereby three dimensional remodeling of vascular tubes creates a functional new microcirculatory network. As part of this response, proteolytic enzymes, including matrix metalloproteinases (MMPs), are released by endothelial cells to disrupt interactions with neighboring cells, facilitating endothelial cell adhesion, migration, and growth factor signaling through the dynamic modulation of integrin receptor expression (3).

In chronic wounds, however, normal healing processes including angiogenesis are disrupted, resulting in delayed or inappropriate healing. Chronic wounds often occur in the presence of systemic diseases such as diabetes and atherosclerosis, which are accompanied by microvascular deficiencies (2). Moreover, a number of cellular and molecular defects are associated with poor healing of chronic wounds, including growth factor signaling, imbalances of MMPs and tissue inhibitors of metalloproteinases (TIMPs), and impaired recruitment of progenitor cells, suggesting that the correction of these abnormalities may promote a more natural healing process (1,4).

Human amniotic membranes have been successfully used to treat chronic cutaneous wounds (5-8). Allografts derived from human amniotic membrane exhibit low immunogenicity and have shown the ability to reduce inflammation, pain, and scarring, and accelerate wound healing (9-17).

Beyond serving as a protective wound barrier, human amniotic membrane provides a biological matrix supporting cell proliferation and tissue ingrowth. Growth factors that play a role in normal wound healing have also been identified in both fresh and preserved amniotic tissues, including epidermal growth factor (EGF), bFGF, keratinocyte growth factor (KGF), TGF-α and -β, hepatocyte growth factor (HGF), and nerve growth factor (NGF) (18-20). We thus hypothesized that one mechanism by which amniotic membrane therapy accelerates wound healing is through induction of angiogenesis.

To ensure that safely harvested amniotic tissue allografts preserve their bioactivity for clinical application, are stable for long-term storage, and are available for off the shelf use, MiMedx Group, Inc. (Marietta, Ga., USA) has developed a gentle cleansing and dehydration process (PURION® process), described elsewhere (21-23). PURION® processed and dehydrated human amnion/chorion membrane (dHACM) allografts have recently been shown to contain a multitude of pro-angiogenic growth factors beyond those listed above, including PDGF-AA, PDGF-BB, P1GF, granulocyte colony-stimulating factor (GCSF), and VEGF, among others (24).

The goal of this study was to determine the ability of PURION® processed and dehydrated human amnion/chorion membrane (dHACM) allografts to promote angiogenesis. A thorough characterization of the angiogenesis-related growth factors within EpiFix® dHACM advanced wound care product (MiMedx Group, Inc.) was performed. To examine the ability of dHACM to modulate endothelial cell behavior, human endothelial cell proliferation, migration, and their production of endogenous angiogenic factors in vitro in response to dHACM was determined. In vivo studies were further conducted to determine the ability of dHACM to promote angiogenesis in a murine subcutaneous implantation model.

Abbreviations in Example 1

AATB: American Association of Tissue Banks; ANG-2: angiopoietin-2; APLAC: Administrative Panel on Laboratory Animal Care; bFGF/FGF2: basic fibroblast growth factor; CMV: cytomegalovirus; DAPI: 4', 6-diamidino-2-phenylindole; dHACM: dehydrated human amnion/chorion membrane; ECM: extracellular matrix; EGF: epidermal growth factor; ELISA: enzyme-linked immunosorbent assays; FDA: Food and Drug Administration; GCSF: granulocyte colony-stimulating factor; HB-EGF: heparin binding epidermal growth factor; HGF: hepatocyte growth factor; HIV: human immunodeficiency virus; HMVEC: human microvascular endothelial cell; HTLV: human T-lymphotropic virus; HUVEC: human umbilical vein endothelial cell; IL: interleukin; KGF: keratinocyte growth factor; MMP: matrix metalloproteinase; NGF: nerve growth factor; PDGF: platelet derived growth factor BB; P1GF: placental growth factor; TGF: transforming growth factor 13; TIMP: tissue inhibitor of metalloproteinases; VEGF: vascular endothelial growth factor; VEGF-R2: VEGF receptor 2.

Methods

Dehydrated Human Amnion/Chorion Membrane (dHACM)

dHACM is a dehydrated human allograft comprised of laminated amnion and chorion membranes derived from the placenta (21-23). Human placentas were donated under informed consent following Cesarean sections, as regulated by the Food and Drug Administration's (FDA) Good Tissue Practice and American Association of Tissue Banks (AATB). All donors were tested to be free of infectious diseases, including human immunodeficiency virus (HIV), human T-lymphotropic virus (HTLV), hepatitis B and C, syphilis, and cytomegalovirus (CMV). Amnion and chorion were isolated from placenta, processed with the proprietary PURION® process that involves gentle cleansing of the layers, and then laminated to form the graft, which was dehydrated under controlled drying conditions (23). A specific version of dHACM (EpiFix®, MiMedx Group) was used as the test material in this study; therefore, the results of this study apply only to PURION® processed dehydrated human amnion/chorion composite grafts (dHACM).

ELISA Assays

The content of angiogenic growth factors in samples of processed, dehydrated human amnion/chorion grafts (dHACM) from eight donors was measured with standard enzyme-linked immunosorbent assays (ELISAs; RayBiotech, Inc., Norcross, Ga.). Weighed, minced dHACM samples were placed in lysis buffer containing protease inhibitors for 24 hours at 4° C. Samples were then homogenized, centrifuged to remove tissue residue, and the amount of specific angiogenic factors in the lysis buffer was measured in diluted aliquots with standard ELISA assays. Growth factor content was normalized to the dry mass of starting tissue.

In Vitro Proliferation of Human Microvascular Endothelial Cells

To prepare extracts of dHACM for cell culture experiments, sterilized grafts were minced and extracted in Medium 131, with and without supplement, at a concentration of 20 milligrams of tissue per milliliter of medium. After 24 hours of extraction at 4° C., the tissue residue was removed by centrifugation and the extract was sterile filtered. Previous studies have established that a significant amount of the growth factors and cytokines in dHACM elute from the tissue under these conditions (24).

Human microvascular endothelial cells (HMVECs; Gibco, Life Technologies Corp. C011-5C, Carlsbad, Calif.) from adult dermis were plated on 96-well plates for 24 hours in Medium 131 with Microvascular Growth Supplement (Gibco, Life Technologies Corp. S-005-25). The Microvascular Growth Supplement was comprised of growth factors, hormones, and tissue extracts necessary for culture of HMVECs, and the final concentration of supplements in Medium 131 was 4.9% v/v fetal bovine serum, 1 iug/mL hydrocortisone, 3 ng/mL human fibroblast growth factor, 10 ug/mL heparin, 1 ng/mL human epidermal growth factor, and 0.08 mM dibutyryl cyclic AMP. After 24 hours to allow for cell adhesion, the medium was aspirated from the wells and replaced with one of the following: medium lacking supplement (negative control), medium plus supplement (positive control), or medium containing extracts of dHACM at 2 mg/mL, 1 mg/mL, or 0.5 mg/mL, both with and without supplement. After 72 hours, the plate was washed to remove unattached cells and a CyQuant assay (Molecular Probes, Life Technologies Corp. C7026) was performed to quantify DNA content (n=5). DNA content was translated to cell number, using a standard curve of known cells as determined by counting on a hemocytometer.

In Vitro Production of Angiogenic Growth Factors by Human Microvascular Endothelial Cells Human microvascular endothelial cells were cultured as described above in Medium 131 with Microvascular Growth Supplement for 24 hours on 96-well plates at a density of 3500 cells/well. Following 24-hour culture to allow for cell adhesion, the cells were treated with dHACM extract in Medium 131 with supplement at 2, 1, and 0.5 mg/mL concentrations. After 72-hour treatment, the supernatant from 5 wells per sample group was recovered and tested for the presence of 60 growth factors, cytokines, and soluble growth factor receptors. Quantibody assays (Angiogenesis Array 1000, RayBiotech, Norcross, Ga.) were performed on the supernatant according to the manufacturer's instructions and were quantified using a fluorescent microarray scanner (GenePix 4000B, Molecular Devices, Sunnyvale, Calif.). A CyQuant assay was subsequently performed, as described above, on the adherent cells to determine cell number.

In Vitro Transwell Migration Studies with Human Umbilical Vein Endothelial Cells Using a modified Boyden chamber assay, human umbilical vein endothelial cells (HUVECs) were assayed for chemotactic cell migration toward dHACM tissue. Migration assays were performed in 24-well transwell inserts with 8 [tm pore membrane filters (Corning, Corning, N.Y.). 600 μL of supplement-free culture medium was loaded into the bottom wells, followed by the addition of differently sized portions of dHACM tissue, including 2.0 and 6.0 mm diameter disks (n=4 dHACM tissue donors tested). Supplement-free Medium 200 (basal medium; Gibco, Life Technologies Corp. M-200-500) and Medium 200 containing Large Vessel Endothelial Supplement (complete medium; Gibco, Life Technologies Corp. A14608-01) acted as negative and positive controls, respectively (n=4). The Large Vessel Endothelial Supplement contains fetal bovine serum, hydrocortisone, human epidermal growth factor, human basic fibroblast growth factor, heparin, and ascorbic acid, optimized for culture of HUVECs (Gibco, Life Technologies Corp. C-003-5C). $3.3 \times 10^4$ HUVECs (passage 5) were seeded into the transwell inserts in 100 pl basal medium and cultured for 24 hours to permit migration.

After 24 hours, both sides of the inserts were rinsed with PBS, and non-migrating cells were removed with a cotton-tipped swab. Remaining cells were fixed in 4% formaldehyde in PBS for 30 minutes, and stained with 4',6-diamidino-2-phenylindole (DAPI) for 5 minutes prior to imaging in PBS on a fluorescence microscope (EVOS FL Auto, 10× objective, Life Technologies). Migrated cells were counted and averaged across four micrographs per insert.

dHACM Implantation and Tissue Harvest

Murine experiments conducted at Stanford were approved by the Administrative Panel on Laboratory Animal Care (APLAC), protocol #20627. dHACM products from six donors were utilized in a simple subcutaneous implant model. Briefly, 4-month-old C57BL/6J mice (Jackson Laboratories, Bar Harbor, Me.) were anesthetized and prepped before a horizontal 6 mm incision was created on the dorsum. A subcutaneous pocket was bluntly dissected in the fascial plane underlying the panniculus carnosus, and a 5×5 mm square of dHACM was surgically placed. At days 3, 7, 14, and 28 post operation, a representative cohort of mice was sacrificed, and the implant and overlying skin were harvested for histological analysis. Uninjured skin was also collected as a reference for normal cutaneous vascularity.

Histological Analysis of Implant Neovascularization

Tissue was harvested and embedded in OCT (Sakura Finetek USA, Inc., Torrance, Calif., USA). 10 [im thick frozen sections were fixed in acetone and immunostained using an antibody against CD31 (1:200, Abcam, Cambridge, Mass., USA). Nuclei were stained with DAPI. Microvessel counts were conducted on intra-implant high power fields (400×) following CD31 staining.

Statistical Analyses

Statistical comparisons were performed by using two-tailed, unpaired Student's t-tests with significance set at $p \leq 0.05$ to compare treatment groups to their respective controls. All values were expressed as the mean±standard deviation.

Results

Angiogenic Factors in dHACM

ELISAs performed on dHACM samples showed quantifiable levels of the following angiogenic growth factors:

angiogenin, angiopoietin-2 (ANG-2), epidermal growth factor (EGF), basic fibroblast growth factor (bFGF), heparin binding epidermal growth factor (HB-EGF), hepatocyte growth factor (HGF), leptin, platelet derived growth factor BB (PDGF-BB), placental growth factor (P1GF), and vascular endothelial growth factor (VEGF). The amount of each factor was normalized to the starting dry weight of the tissue (Table I).

TABLE I

Angiogenic growth factor and cytokine content in dHACM grafts (n = 8 donors)

|  | Average Content (pg/mg of dry tissue) | Standard Deviation |
|---|---|---|
| Angiogenin | 89.410 | 10.504 |
| Angiopoietin-2 (ANG-2) | 22.201 | 27.471 |
| EGF | 6.018 | 3.852 |
| bFGF | 0.717 | 0.225 |
| HB-EGF | 0.651 | 0.064 |
| HGF | 245.418 | 103.302 |
| Leptin | 0.628 | 0.000 |
| PDGF-BB | 96.109 | 29.057 |
| PlGF | 2.396 | 0.953 |
| VEGF | 11.091 | 14.243 |

Endothelial Cell Proliferation

The human dermal microvascular endothelial cells proliferated to a minor extent in supplement-free medium (negative control), whereas inclusion of Microvascular Growth Supplement in the positive control wells caused the cells to nearly double in number (FIG. 1). Extracts of dHACM caused proliferation of HMVECs in culture. At all concentrations of the extract, cells proliferated to a significantly greater extent than their respective controls ($p<0.05$) with or without supplement. There was no dose response observed among the three extract concentrations, indicating the maximum response was achieved with these concentrations.

Growth Factor Production by Microvascular Endothelial Cells

Figure 2:
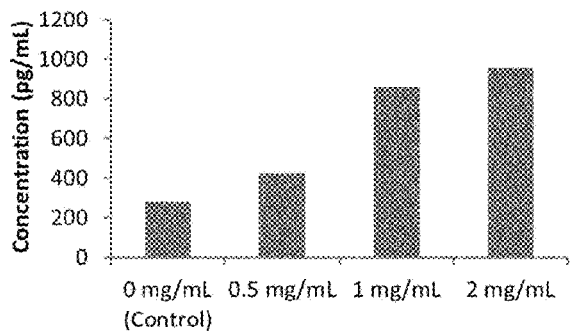
FIG. 2, panels A-F show a change in growth factor production by human microvascular endothelial cells when cultured in the presence of varying concentrations of dHACM extract. Endothelial cells increased production of angiogenin, HB-EGF, PDGF-BB, IL-2, IL-2, and IL-8 in a dose dependent manner when cultured in the presence of dHACM extract, compared to untreated cells cultured without extract.
Figure 2:
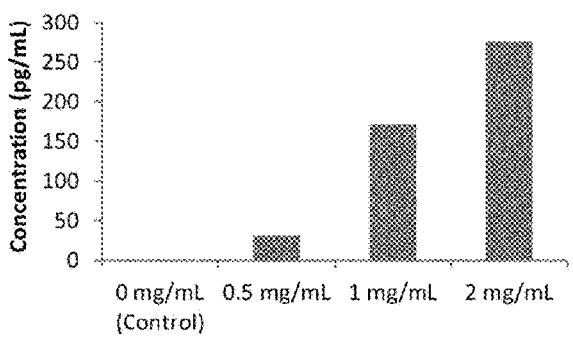
Figure 2:
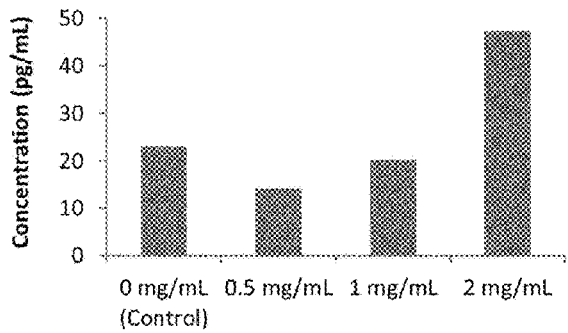
Figure 2:
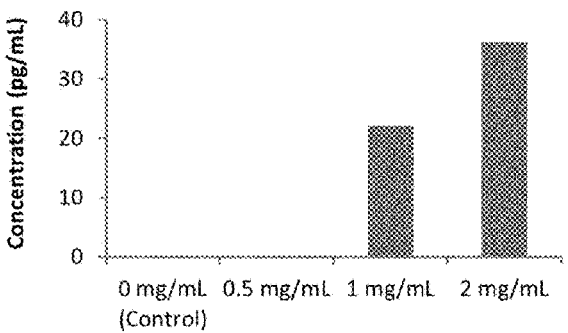
Figure 2:
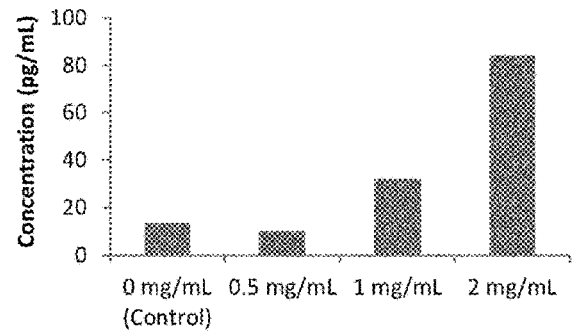
Figure 2:
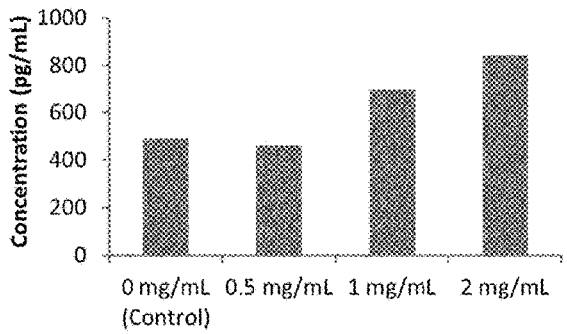

The effect of dHACM on growth factor production by microvascular endothelial cells was examined by treating cells with extracts of dHACM for three days and measuring the amount of each growth factor in the culture medium at the end of the culture period. Since the extract caused endothelial cells to proliferate as shown in FIG. 2, cell number was measured in each well after the culture medium was collected, and growth factor values were normalized on a per cell number. The amount of each growth factor in the extract itself was also measured and subtracted from that in the medium to calculate the amount of additional growth factor produced by the HMVECs themselves.

Figure 3:
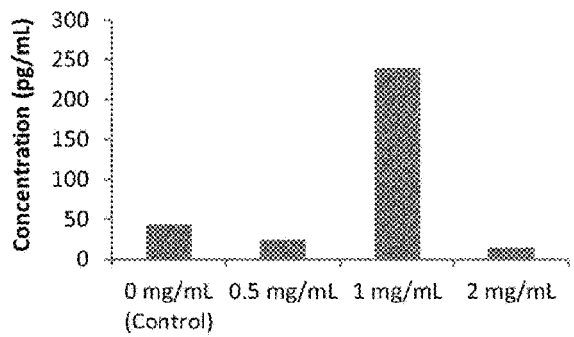
FIG. 3, panels A-F show a change in growth factor production by human microvascular endothelial cells when cultured in the presence of varying concentrations of dHACM extract. Endothelial cells increased production of TGF-α, TGF-β, VEGF, angiopoietin-1, and angiostatin when cultured in the presence of 1 mg/mL dHACM extract and increased production of VEGF receptor 2 in 0.5 mg/mL dHACM extract, compared to untreated cells cultured without extract; however, a dose response was not observed at higher concentrations for these cytokines.
Figure 3:
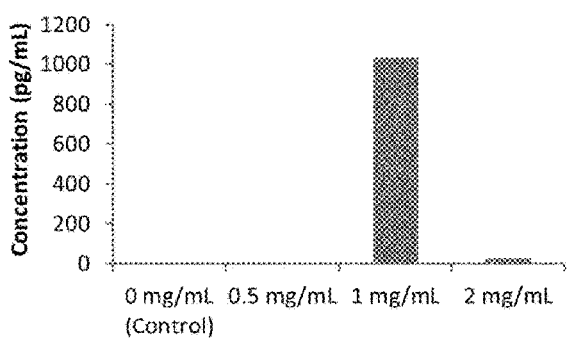
Figure 3:
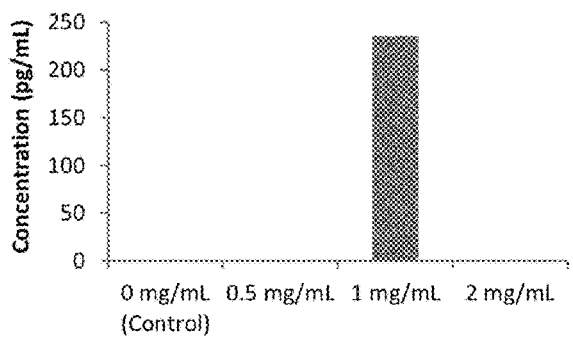
Figure 3:
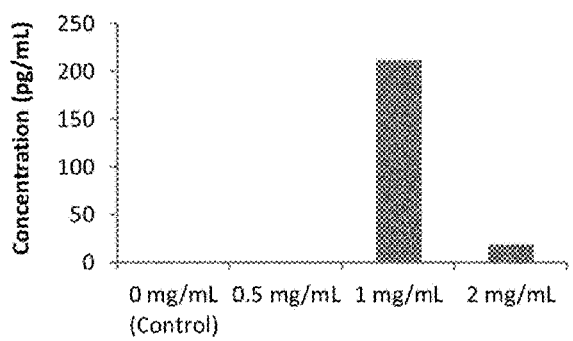
Figure 3:
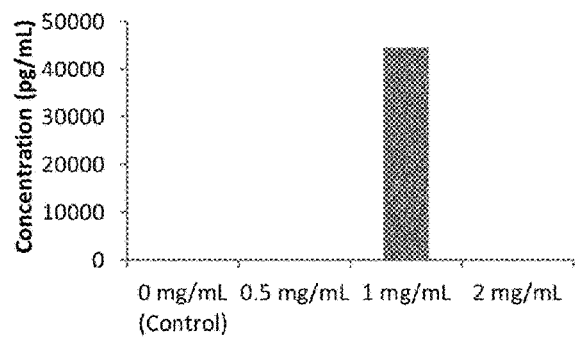
Figure 3:
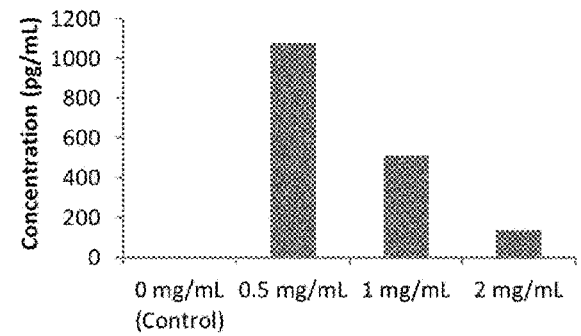

The induction of specific growth factor production by endothelial cells in culture caused by extracts of dHACM is shown in FIG. 2 and FIG. 3. HMVECs increased production of angiogenin, HB-EGF, PDGF-BB, interleukin-2 (IL-2), IL-6, and IL-8 in a dose dependent manner when cultured in the presence of dHACM extract, compared to untreated cells cultured without extract. FIG. 2. HMVECs also greatly increased production of TGF-α, TGF-β3, VEGF, angiopoietin-1, and angiostatin when cultured in the presence of 1 mg/mL dHACM extract and increased production of VEGF receptor 2 (VEGF-R2) in 0.5 mg/mL dHACM extract. FIG. 3. A dose response was not observed at higher concentrations for each of these cytokines. It is likely that due to the numerous cytokines present in the dHACM grafts, as well as their diverse downstream functions, conflicting signaling pathways were subsequently activated by dHACM extracts resulting in the peak response observed in FIG. 3. While a large array of 60 angiogenic factors were assayed in this experiment, for simplicity, only a subset of 12 notable factors were reported here.

Effects of dHACM on HUVEC Migration In Vitro

Figure 4:
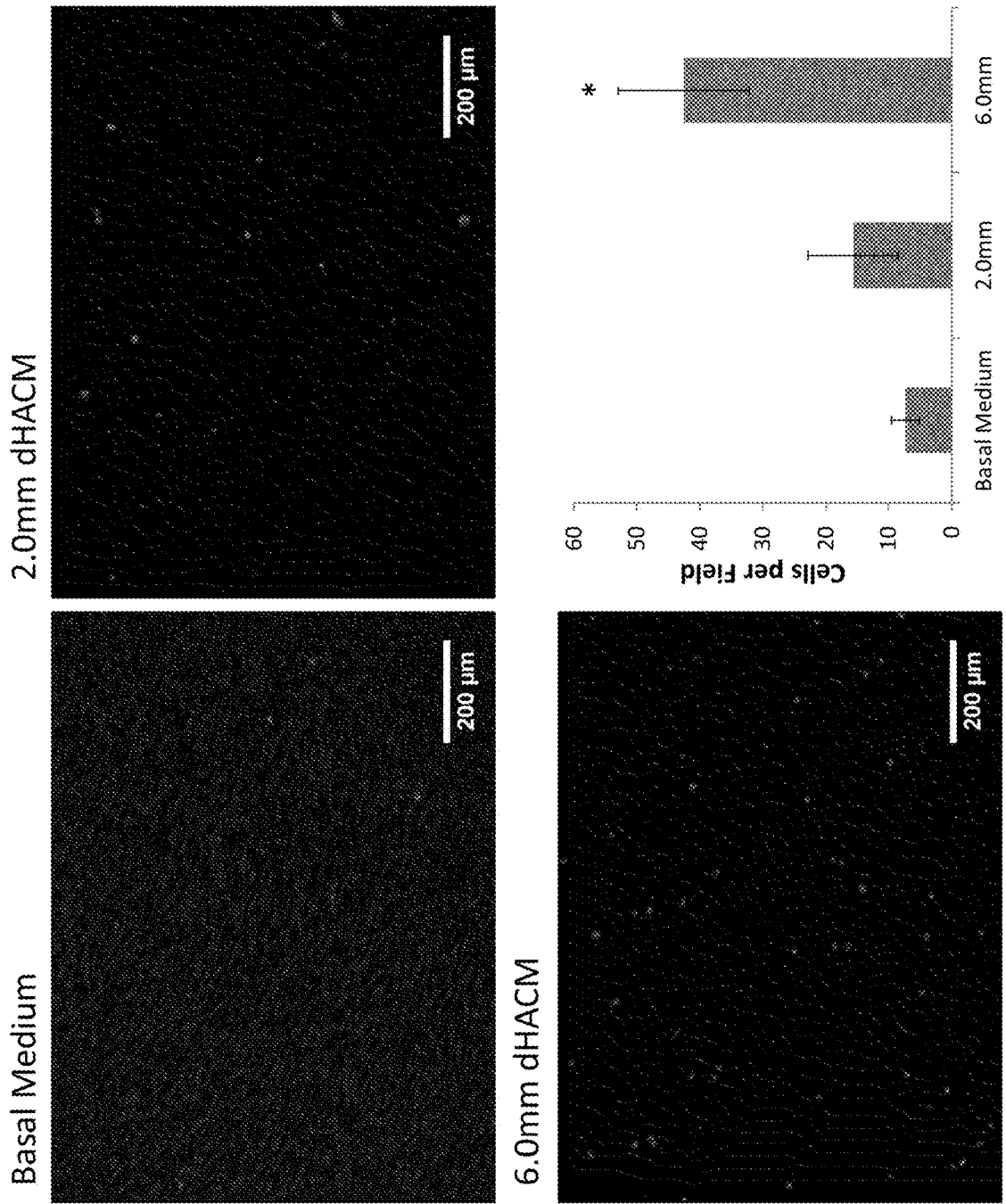
FIG. 4 demonstrates the average number of migrated human umbilical vein endothelial cells (HUVECs) per field of view in response to dehydrated human amnion/chorion tissue allografts (dHACM). Representative micrographs and cell counts indicated that greater migration was observed in response to larger samples, relative to their smaller counterparts. HUVEC migration in complete medium was significantly greater than all other samples (p≤0.05). * indicates significantly greater migration than basal medium and 2.0 mm groups (p≤0.05). Scale bar—200 μm.

HUVEC migration in the basal medium and the smallest 2.0 mm samples was not significantly different; however, samples containing 6.0 mm diameter disks of dHACM tissue demonstrated significantly greater migration compared with basal medium and 2.0 mm samples FIG. 4. No experimental group reached the number of cells comparable to complete medium (260±68 cells per field); however, the 6.0 mm diameter samples demonstrated that dHACM tissue in the culture medium was capable of directing endothelial cell migration in vitro.

Neovascular Response to dHACM Following In Vivo Implantation

Figure 5:
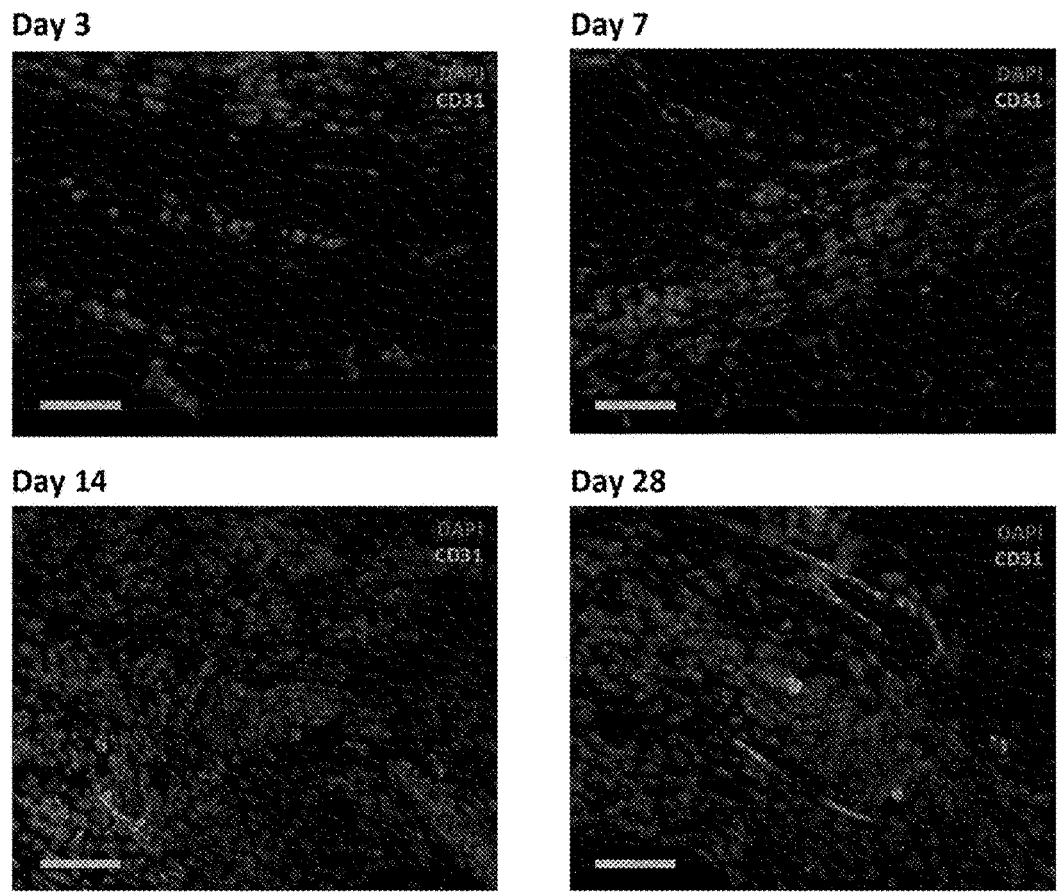
FIG. 5 depicts the neovascular response following in vivo dHACM implantation. An increasing number of CD31 positive microvessels were seen within the implanted dHACM over time, ultimately reaching the level of normal skin by day 28. Scale bar—50 gm.
Figure 5:
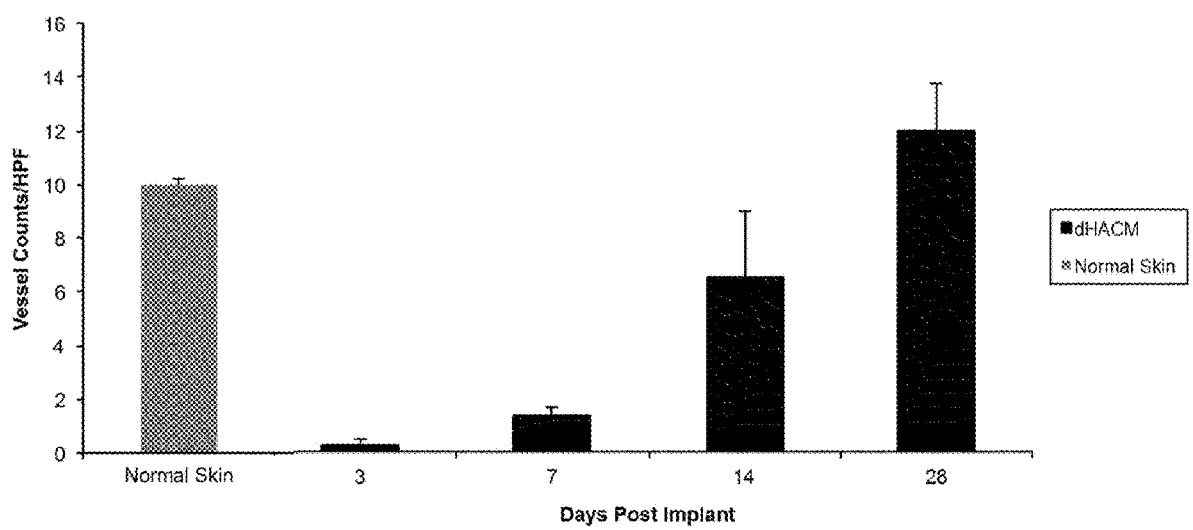

Immunohistochemical staining for the endothelial cell specific antigen CD31 was performed to characterize the neovascular response within implanted dHACM grafts. The quantity of CD31 positive microvessels were found to steadily increase through day 28, indicative of dynamic intra-implant neovascularization. FIG. 5.

Discussion

These studies clearly demonstrate that dehydrated human amnionichorion membranes (dHACM) contain a large number of pro-angiogenic growth factors, including angiogenin, angiopoietin-2, EGF, bFGF, HB-EGF, HGF, leptin, PDGF-BB, P1GF, and VEGF. This partial list of growth factors does not encompass the entire array of physiologically important and biologically active molecules present in dHACM (24). These particular growth factors, however, are likely to be responsible for the clinical benefits of this dHACM allograft, in relation to neovascularization and healing within chronic wounds. These soluble signals in dHACM also stimulated human microvascular endothelial cells to proliferate in vitro, and further, to increase production of endogenous growth factors, cytokines, and receptors related to angiogenesis, including angiogenin, angiopoietin-1 (ANG-1), angiostatin, HB-EGF, PDGF-BB, VEGF, and VEGF receptor 2. Furthermore, dHACM tissue promoted chemotactic migration of human endothelial cells in vitro, suggesting that these soluble factors are capable of recruiting endothelial cells to promote wound re-vascularization. These findings strongly support dHACM exerting therapeutic actions both directly and indirectly by activating multiple signaling pathways that promote angiogenesis within healing wounds.

Previous work demonstrated that PURION® processed dHACM tissue also retains a collection of growth factors, anti-inflammatory molecules, and tissue inhibitors of metalloproteinases that play other important roles in wound healing. Specifically, this material or its extracts, promoted the proliferation of dermal fibroblasts and the recruitment of progenitor cells in vitro and in vivo (24). Combined with the present results, dHACM allografts contain a wide array of soluble signals, only a fraction of which have been identified to date, which may stimulate healing through a variety of signaling pathways and physiological mechanisms.

These multifunctional mechanisms offer advantages for dHACM as a treatment of difficult to heal chronic wounds. In normal wounds, the initial fibrin clot acts as both a matrix for repair and as a reservoir for growth and cell recruitment factors (25). Inflammatory cells, including neutrophils, monocytes, and lymphocytes then invade the wound and release further growth factors and cytokines that initiate wound repair machinery, including keratinocyte and fibroblast migration/proliferation, microvascular endothelial cell recruitment, proliferation, and angiogenesis, and nerve sprouting within the granulation tissue (25). In chronic wounds, however, including diabetic and venous ulcers characterized by deficiencies in vascularization and cytokine signaling, the exogenous delivery of key cytokines and growth factors may be necessary to restore a molecular balance and achieve healing (26).

Single growth factors may be insufficient to overcome to multiple deficiencies in most chronic wounds, as demonstrated by the modest efficacy and limited utility of recombinant human PDGF (becaplermin) as a single agent as shown in a meta-analysis of well-designed clinical trials (27). By contrast, dHACM contains additional angiogenic factors, specifically VEGF and bFGF (FGF2), both potent angiogenic cytokines that promote endothelial cell proliferation and migration (28). We also identified PIGF which not only as directs angiogenic effects, but acts synergistically with VEGF to stimulate wound angiogenesis (29). The growth factors angiopoietin-1 and 2 are critical for regulating the stabilization and remodeling of blood vessels (25, 28). It was found that dHACM also stimulates human microvascular endothelial cells to increase production of a variety of angiogenic cytokines and growth factors suggests this material's ability to amplify the initial signals provided by the allograft itself, potentially even beyond the lifespan of the allograft.

Previous studies of amniotic membranes in regulating angiogenesis have reported conflicting data, with some describing enhanced vascularization while others have observed inhibition of angiogenesis. Anti-angiogenic effects have been widely reported in cases of ocular/corneal surgery (30), while improved vascularization and healing have been reported when used to promote healing of cutaneous wounds (31, 32). This dichotomy may be explained in part by the presence of both anti-angiogenic (including thrombospondin-1, endostatin, and anti-angiogenic TIMPs) (33) and pro-angiogenic factors (including VEGF and PDGF) (34, 35) in amniotic tissues. Combined with the previously described role of the local environment in regulating angiogenesis, the specific response to the amniotic membrane graft cytokine milieu may thus be largely dependent on the target tissue and the location of the implantation.

In this study, subcutaneous implantation of dHACM tissues in a murine model demonstrated a steady increase in vascularization through day 28. These results are in line with the in vitro findings, and consistent with the time course of clinical trial data (17), supporting the retention of biological activity by growth factors present in PURION® processed dHACM grafts. The prolonged pro-angiogenic effects from a single implant may offer potential practical benefits compared to advanced wound interventions that require more frequent (daily or biweekly) applications.

The clinical value of dHACM grafts for use as therapy in non-healing wounds has been demonstrated by clinical research, even as further translational studies are underway. Treatment with dHACM allografts was reported to improve healing in patients with a variety of wound types for which traditional therapies were ineffective (13). Additionally, refractory wounds that healed after dHACM treatment were reported not to recur with long-term follow-up (14). Finally, in a small, prospective, randomized clinical trial, Zelen et al. demonstrated a significant increase in the healing rate of diabetic foot ulcers treated with dHACM compared to those treated with a standard therapeutic regimen, with 77% and 92% of dHACM wounds healed at week 4 and 6, compared to only 0% and 8% of controls (27). The aggregate data of dHACM suggests this material could be studied for comparative effectiveness with other available wound healing products.

In summary, dHACM allografts derived from human placenta contain multiple angiogenic growth factors with retained biological activity, directly stimulate angiogenesis, and encourage amplification of angiogenic signaling cues by inducing production of endogenous growth factors from human endothelial cells in vitro. The angiogenic effects are prolonged to at least 28 days. These properties help explain the effectiveness of dHACM reported in clinical studies, and suggest the potential of dHACM grafts to promote revascularization and healing within poorly vascularized, non-healing wounds and other tissues.

REFERENCES

1. Blakytny R, Jude E: The molecular biology of chronic wounds and delayed healing in diabetes. *Diabetic medicine: a journal of the British Diabetic Association* 2006, 23:594608.
2. Bauer S M, Bauer R J, Velazquez O C: Angiogenesis, vasculogenesis, and induction of healing in chronic wounds. *Vascular and endovascular surgery* 2005, 39:293-306.
3. Tonnesen M G, Feng X, Clark R A: Angiogenesis in wound healing. *The journal of investigative dermatology Symposium proceedings/the Society for Investigative Dermatology, Inc [and] European Society for Dermatological Research* 2000, 5:40-46.
4. Kim K A, Shin Y J, Kim J H, Lee H, Noh S Y, Jang S H, Bae O N: Dysfunction of endothelial progenitor cells under diabetic conditions and its underlying mechanisms. *Archives of pharmacal research* 2012, 35:223-234.
5. Mermet I, Pottier N, Sainthillier J M, Malugani C, Cairey-Remonnay S, Maddens S, Riethmuller D, Tiberghien P, Humbert P, Aubin F: Use of amniotic membrane transplantation in the treatment of venous leg ulcers. *Wound repair and regeneration: official publication of the Wound Healing Society [and] the European Tissue Repair Society* 2007, 15:459-464.
6. Subrahmanyam M: Amniotic membrane as a cover for micro skin grafts. *British journal of plastic surgery* 1995, 48:477-478.
7. John T: Human amniotic membrane transplantation: past, present, and future. *Ophthalmology clinics of North America* 2003, 16:43-65, vi.
8. Gruss J S, Jirsch D W: Human amniotic membrane: a versatile wound dressing. *Canadian Medical Association journal* 1978, 118:1237-1246.
9. Kubo M, Sonoda Y, Muramatsu R, Usui M: Immunogenicity of human amniotic membrane in experimental xenotransplantation. *Investigative ophthalmology & visual science* 2001, 42:1539-1546.
10. Ueta M, Kweon M N, Sano Y, Sotozono C, Yamada J, Koizumi N, Kiyono H, Kinoshita S: Immunosuppressive properties of human amniotic membrane for mixed lymphocyte reaction. *Clinical and experimental immunology* 2002, 129:464-470.
11. Dua H S, Gomes J A, King A J, Maharajan V S: The amniotic membrane in ophthalmology. *Survey of ophthalmology* 2004, 49:51-77.

12. Toda A, Okabe M, Yoshida T, Nikaido T: The potential of amniotic membrane/amnion-derived cells for regeneration of various tissues. *Journal of pharmacological sciences* 2007, 105:215-228.
13. Forbes J, Fetterolf D E: Dehydrated amniotic membrane allografts for the treatment of chronic wounds: a case series. *Journal of wound care* 2012, 21:290, 292, 294-296.
14. Sheikh E S, Sheikh E S, Fetterolf D E: Use of dehydrated human amniotic membrane allografts to promote healing in patients with refractory non healing wounds. *International wound journal* 2013.
15. Serena T, Fetterolf D E: Clinical Research: Dehydrated human amniotic membrane (dHAM) treatment of lower extremity venous ulceration (CR23). In *SAWC Annual Spring Meeting; Atlanta, Ga.* 2012.
16. Ennis W, Sui A, Papineau E: Clinical experience with a novel regenerative template for hard to heal wounds. In *SAWC Annual Spring Meeting; Atlanta, Ga.* 2012.
17. Zelen C M, Serena T E, Denoziere G, Fetterolf D E: A prospective randomised comparative parallel study of amniotic membrane wound graft in the management of diabetic foot ulcers. *International wound journal* 2013, 10:502-507.
18. Lopez-Valladares M J, Teresa Rodriguez-Ares M, Tourino R, Gude F, Teresa Silva M, Couceiro J: Donor age and gestational age influence on growth factor levels in human amniotic membrane. *Acta ophthalmologica* 2010, 88:e211-216.
19. Russo A, Bonci P, Bonci P: The effects of different preservation processes on the total protein and growth factor content in a new biological product developed from human amniotic membrane. *Cell and tissue banking* 2012, 13:353-361.
20. Koizumi N J, Inatomi T J, Sotozono C J, Fullwood N J, Quantock A J, Kinoshita S: Growth factor mRNA and protein in preserved human amniotic membrane. *Current eye research* 2000, 20:173-177.
21. Daniel J, Tofe R, Spencer R, Russo J: Placental tissue grafts. 2008, U.S. Pat. No. 8,357,403.
22. Daniel J: Placental tissue grafts. 2007, U.S. Pat. No. 8,372,437.
23. Daniel J, Tofe R, Spencer R, Russo J: Placental tissue grafts. 2012, U.S. Pat. No. 8,409,626.
24. Koob T J, Rennert R, Zabek N, Massee M, Lim J J, Temenoff J S, Li W W, Gurtner G: Biological properties of dehydrated human amnionichorion composite graft: implications for chronic wound healing. *International wound journal* 2013, 10:493-500.
25. Werner S, Grose R: Regulation of wound healing by growth factors and cytokines. *Physiological reviews* 2003, 83:835-870.
26. Wieman T J, Smiell J M, Su Y: Efficacy and safety of a topical gel formulation of recombinant human platelet-derived growth factor-BB (becaplermin) in patients with chronic neuropathic diabetic ulcers. A phase III randomized placebo-controlled double-blind study. *Diabetes care* 1998, 21:822-827.
27. Smiell J M, Wieman T J, Steed D L, Perry B H, Sampson A R, Schwab B H: Efficacy and safety of becaplermin (recombinant human platelet-derived growth factor-BB) in patients with nonhealing, lower extremity diabetic ulcers: a combined analysis of four randomized studies. *Wound repair and regeneration: official publication of the Wound Healing Society [and] the European Tissue Repair Society* 1999, 7:335-346.
28. Li J, Zhang Y P, Kirsner R S: Angiogenesis in wound repair: angiogenic growth factors and the extracellular matrix. *Microscopy research and technique* 2003, 60:107-114.
29. Carmeliet P, Moons L, Luttun A, Vincenti V, Compernolle V, De Mol M, Wu Y, Bono F, Devy L, Beck H, et al: Synergism between vascular endothelial growth factor and placental growth factor contributes to angiogenesis and plasma extravasation in pathological conditions. *Nature medicine* 2001, 7:575-583.
30. Kim J C, Tseng S C: The effects on inhibition of corneal neovascularization after human amniotic membrane transplantation in severely damaged rabbit corneas. *Korean journal of ophthalmology: KJO* 1995, 9:32-46.
31. Bennett J P, Matthews R, Faulk W P: Treatment of chronic ulceration of the legs with human amnion. *Lancet* 1980, 1:1153-1156.
32. Faulk W P, Matthews R, Stevens P J, Bennett J P, Burgos H, Hsi B L: Human amnion as an adjunct in wound healing. *Lancet* 1980, 1:1156-1158.
33. Hao Y, Ma D H, Hwang D G, Kim W S, Zhang F: Identification of antiangiogenic and anti-inflammatory proteins in human amniotic membrane. *Cornea* 2000, 19:348-352.
34. Steed D L, Trumpower C, Duffy D, Smith C, Marshall V, Rupp R, Robson M: Amnion-derived cellular cytokine solution: a physiological combination of cytokines for wound healing. *Eplasty* 2008, 8:e18.
35. Uberti M G, Pierpont Y N, Ko F, Wright T E, Smith C A, Cruse C W, Robson M C, Payne W G: Amnion-derived cellular cytokine solution (ACCS) promotes migration of keratinocytes and fibroblasts. *Annals of plastic surgery* 2010, 64:632-635.

All references cited herein are incorporated by reference into this application in their entirety.

What is claimed is:

1. A method for inducing angiogenesis in a non-cardiovascular body region of a subject having diabetic peripheral neuropathy, said method comprising delivering an effective amount of a composition comprising modified placental tissue to said non-cardiovascular body region, wherein said modified placental tissue comprises an amnion layer having an epithelial layer which has not been substantially removed.

2. The method of claim 1, wherein blood flow to the non-cardiovascular body region is restricted.

3. The method of claim 1, wherein the non-cardiovascular body region includes peripheral portions of the body, liver, lung, nerve, bone, or skin.

4. The method of claim 3, wherein the peripheral portions of the body are limbs, hands, or feet.

5. The method of claim 1, wherein the modified placental tissue further comprises one or more of isolated chorion, intermediate layer, Wharton's jelly, isolated amniotic epithelial layer, or any combination thereof.

6. The method of claim 1, wherein the modified placental tissue is a tissue graft.

7. The method of claim 1, wherein the modified placental tissue is micronized.

8. The method of claim 1, wherein the composition is injectable.

9. The method of claim 1, wherein the composition is a liquid, gel, or paste.

10. The method of claim 1, wherein the composition is administered by a nebulizer.

11. A method for inducing angiogenesis in a non-cardiovascular body region of a subject having diabetic peripheral neuropathy, which method comprises injecting an effective amount of an aqueous solution comprising micronized modified placental tissue to said non-cardiovascular body region and maintaining said region under conditions wherein angiogenesis is induced, wherein said modified placental tissue comprises an amnion layer having an epithelial layer which has not been substantially removed.

12. The method of claim 11, wherein the non-cardiovascular body region includes peripheral portions of the body, liver, lung, nerve, bone, or skin.

* * * * *